US011164239B2

(12) United States Patent
Kumar et al.

(10) Patent No.: US 11,164,239 B2
(45) Date of Patent: Nov. 2, 2021

(54) METHOD, SYSTEM, AND COMPUTER-READABLE STORAGE MEDIUM FOR HETEROGENEOUS DATA STREAM PROCESSING FOR A SMART CART

(71) Applicant: eBay Inc., San Jose, CA (US)

(72) Inventors: Sudeep Kumar, Campbell, CA (US); Deepak Kumar Vasthimal, San Jose, CA (US)

(73) Assignee: eBay Inc., San Jose, CA (US)

( * ) Notice: Subject to any disclaimer, the term of this patent is extended or adjusted under 35 U.S.C. 154(b) by 340 days.

(21) Appl. No.: 15/918,113

(22) Filed: Mar. 12, 2018

(65) Prior Publication Data

US 2019/0279281 A1    Sep. 12, 2019

(51) Int. Cl.
*G06Q 30/00*    (2012.01)
*G06Q 30/06*    (2012.01)
(Continued)

(52) U.S. Cl.
CPC ... *G06Q 30/0641* (2013.01); *G06F 16/24568* (2019.01); *G06Q 30/0631* (2013.01); *G16H 20/60* (2018.01)

(58) Field of Classification Search
None
See application file for complete search history.

(56) References Cited

U.S. PATENT DOCUMENTS 6,283,914 B1    9/2001    Mansfield et al.
8,290,951 B1 *  10/2012   Joa ......................... G06F 16/25
                                                       707/736

(Continued)

FOREIGN PATENT DOCUMENTS

WO    2012/170587 A2    12/2012
WO    2019177922       9/2019

OTHER PUBLICATIONS

Le-Thuy, Tran, An Innovative Method for Monitoring Food Quality and the Healthfulness of Consumers' Grocery Purchases, May 5, 2017, Nutrients, 9, 457 (Year: 2017).*
International Search Report for PCT Application No. PCT/US2019/021531, dated Apr. 30, 2019, 6 pages.
International Written Opinion for PCT Application No. PCT/US2019/021531, dated Apr. 30, 2019, 10 pages.

(Continued)

*Primary Examiner* — Jeffrey A. Smith
*Assistant Examiner* — Timothy J Kang
(74) *Attorney, Agent, or Firm* — Schwegman Lundberg & Woessner, P.A.

(57) ABSTRACT

A network service or application can receive dietary goals or conditions for a user or group of users. The network can determine threshold dietary amounts that users can receive over a predetermined time period to satisfy the goals or conditions. The network can monitor user consumption over the predetermined time period by collecting data from heterogeneous data streams (e.g., data associated with different structures, data types, types of data store, sources, processing rates, etc.), processing the data, storing the data using a distributive processing framework, and exposing optimized views into the data to provide smart virtual shopping cart functionality. The network can evaluate user consumption and food items placed into a virtual shopping cart to determine whether purchasing the items satisfy the thresholds, and if not, issue warnings, provide recommendations for substitute food items, and/or take other appropriate actions.

20 Claims, 16 Drawing Sheets

(51) Int. Cl.
*G16H 20/60* (2018.01)
*G06F 16/2455* (2019.01)

(56) References Cited

U.S. PATENT DOCUMENTS

| | | | |
|---|---|---|---|
| 9,280,640 B2 | 3/2016 | Nusbaum et al. | |
| 9,378,335 B2 | 6/2016 | Bosworth et al. | |
| 10,176,514 B1* | 1/2019 | Chen | G06Q 30/0201 |
| 2005/0113649 A1* | 5/2005 | Bergantino | G06Q 50/22 |
| | | | 600/300 |
| 2005/0240444 A1 | 10/2005 | Wooten et al. | |
| 2006/0199155 A1 | 9/2006 | Mosher | |
| 2009/0075242 A1 | 3/2009 | Schwarzberg et al. | |
| 2010/0240962 A1* | 9/2010 | Contant | A47G 21/02 |
| | | | 600/300 |
| 2012/0102053 A1* | 4/2012 | Barrett | G06F 16/283 |
| | | | 707/754 |
| 2013/0006807 A1* | 1/2013 | Bai | G06Q 30/0643 |
| | | | 705/26.8 |
| 2013/0157232 A1* | 6/2013 | Ehrenkranz | G09B 19/0092 |
| | | | 434/127 |
| 2016/0035248 A1 | 2/2016 | Gibbs | |
| 2016/0086255 A1 | 3/2016 | Sainfort et al. | |
| 2016/0140644 A1 | 5/2016 | Babu et al. | |
| 2017/0364956 A1* | 12/2017 | Dhar | G06Q 30/0261 |
| 2018/0165620 A1* | 6/2018 | Ross | G01G 19/4146 |
| 2019/0122756 A1* | 4/2019 | Paterrov | G06F 16/90324 |

OTHER PUBLICATIONS

International Preliminary Report on Patentability received for PCT Application No. PCT/US2019/021531, dated Sep. 24, 2020, 10 pages.

* cited by examiner

My eBay

Home > My eBay > My Account > Personal Information > My Health

Tabs: Activity | Messages | Account | Health

My eBay Views / My Health
- Health Profile 322A
- Medical 324A
- Diet Plan 326A
- Daily Tracker 328A
- Devices 330A
- Purchases 332
- Preferences 334
- Recipes 336
- Groups 338

Health Profile 322B

| | | |
|---|---|---|
| Age | 35 | Edit |
| Gender | Male | Edit |
| Activity Level | Sedentary | Edit |
| Height | 5 ft. 11 in. | Edit |
| Weight | 225 lb. | Edit |

Medical Information 324B

| | | |
|---|---|---|
| Blood Pressure | 120/80 mmHg | Edit |
| Total Cholestrol | 220 mg/dL | Edit |
| LDL | 100 mg/dL | Edit |
| HDL | 35 mg/dL | Edit |

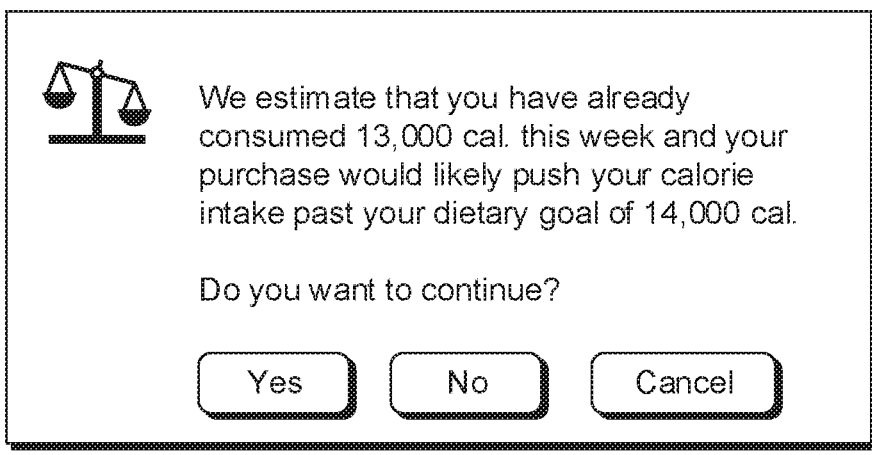
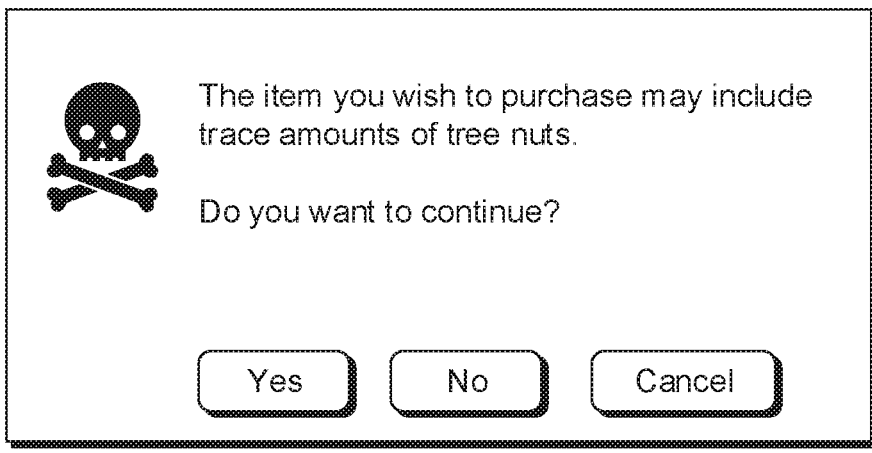
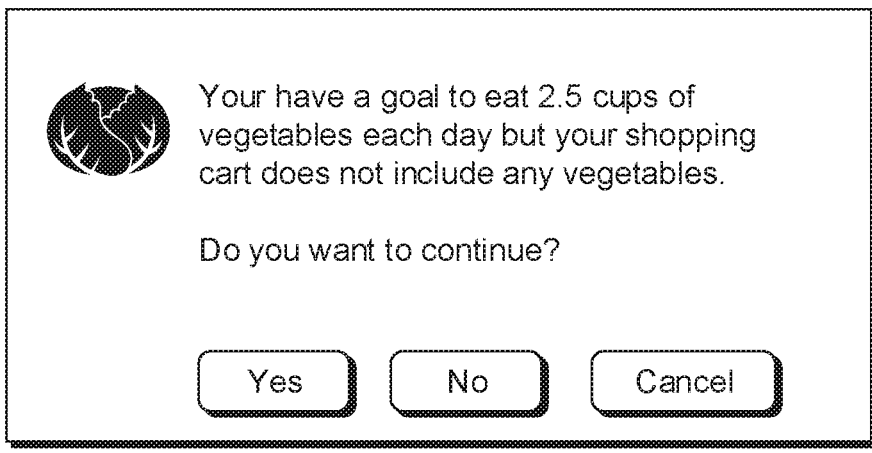
FIG. 3H

FIG. 31

METHOD, SYSTEM, AND COMPUTER-READABLE STORAGE MEDIUM FOR HETEROGENEOUS DATA STREAM PROCESSING FOR A SMART CART

COPYRIGHT NOTICE

A portion of the disclosure of this patent document contains material that is subject to copyright protection. The copyright owner has no objection to the facsimile production by anyone of the patent document or the patent disclosure, as it appears in the Patent and Trademark Office patent files or records, but otherwise reserves all copyright rights whatsoever. The following notice applies to the software and data as described below and in the drawings that form a part of this document: Copyright 2018, eBay Inc. All Rights Reserved.

TECHNICAL FIELD

The subject matter of the present disclosure generally relates to the technology field of heterogeneous data stream processing, and more particularly to heterogeneous data stream processing for providing smart virtual shopping cart functionality.

BACKGROUND

Users have increasingly busy lives, and one of the aspects of their lives they sometimes short-change is their health. One way to maintain good health or to improve one's health is to develop sensible eating habits and planning and preparing wholesome, well-balanced, and nutritious meals. However, it can be difficult to adhere to diet plans or monitor one's progress towards these plans. In some situations, users may have to regularly consult physicians, registered dietitians, and other health professionals or fitness trainers, nutritionists, coaches, and the like to monitor the users and ensure the users are keeping up with their diet plans. But these personal services can come at a great cost of time and expense not available to many users. Other users may rely on software applications that require them to conduct their own research into nutritional information for the food they eat and manually enter this information after every meal. This can be tedious and cumbersome and often becomes neglected such that the users may not be able to keep up with their dietary goals and conditions.

BRIEF DESCRIPTION OF THE DRAWINGS

The present disclosure will describe various embodiments with reference to the drawings, in which:

FIGS. 3A-3I illustrate examples of graphical user interfaces for providing smart virtual shopping cart functionality in accordance with an embodiment

DETAILED DESCRIPTION

Figure 1:
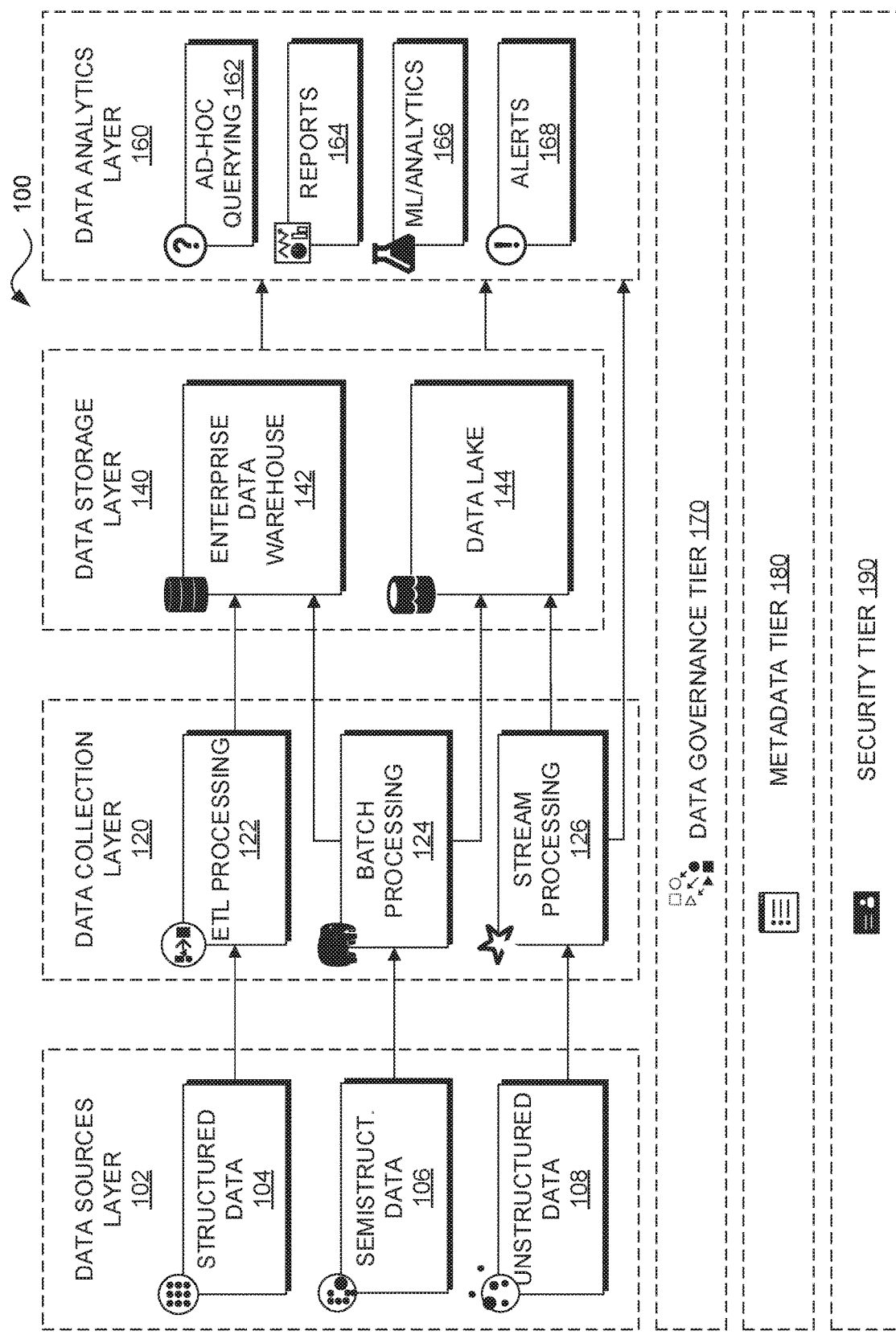
FIG. 1 illustrates an example of a big data system in accordance with an embodiment.

Measures for evaluating well-balanced and nutritious diets exist, such as measures for estimated calorie needs, recommended amounts of food from food groups (e.g., vegetables, fruits, grains, dairy, proteins, oils, etc.), and recommended dietary allowances (RDAS) for macronutrients (e.g., carbohydrates, fiber, fat, etc.), minerals (e.g., calcium, iron, magnesium, etc. and vitamins (e.g., vitamins A, C, D, E, and K, riboflavin, folate, etc.), among others. However, tracking this data is a largely manual process that is monotonous and burdensome for most users. For example, a user may have to determine serving sizes for each food item consumed during a meal, evaluate nutrition fact labels for each processed food item, look up nutrition information for each unprocessed food item, perform a number of arithmetic operations to determine intake amounts, and compare the intake amounts to recommended dietary amounts in order to determine whether just one meal meets the user's dietary goals! Most if not all users do not have the time, patience, and diligence to perform these tasks.

Systems and methods in accordance with various embodiments of the present disclosure overcome these and other deficiencies of conventional approaches for tracking food intake levels and facilitating user adherence to diet plans by integrating smart virtual shopping cart functionality. For illustrative purposes, a network including online marketplace functionality can incorporate this feature. The network can receive dietary goals or conditions for individual users or a group of users (e.g., a family, household, or other group). The network can determine threshold dietary amounts that a user or group of users can receive over a predetermined time period that will satisfy the dietary goals or conditions. The network can monitor the user or group of users' food intake over the predetermined time period based on user information from multiple data streams having widely varying qualities, such as data streams associated with heterogeneous structures (e.g., structured, unstructured, etc.), data types (e.g., text, audio, video, etc.), types of data store (e.g., relational, key-value, document, column family database or data store, etc.), sources (e.g., enterprise systems, social networks, devices and sensors, etc.), and processing rates (e.g., streaming, batch, etc.), among others.

The network can collect, process, and store data from the heterogeneous data streams using a distributive processing framework, such as a massive parallel processing (MPP) framework, the Apache Hadoop® and MapReduce framework, or the Apache Spark™ framework, among others. The network can integrate data from the heterogeneous data streams to provide access to all of the integrated data and to support different modes of access, such as by deploying a hybrid data architecture including an enterprise data warehouse (EDW) and a data lake, a data virtualization architecture, or other multi-model data architecture. The network can provide optimized views (e.g., data marts, operational data stores, analytic sandboxes, etc.) into the integrated data to support the services of the network, such as a smart virtual shopping cart service.

For example, the network can evaluate user food intake over the predetermined time period, the characteristics of food items placed into a virtual shopping cart, and users' dietary goals and conditions to determine whether purchase of the food items would cause users to fail to meet their goals and conditions over the predetermined time period. The network can issue warnings, provide recommendations for substitute food items, and/or improve recommendations for future time periods based on this evaluation. In this manner, the network can help users track their progress toward dietary goals and conditions and support users in meeting these goals and conditions.

Turning now to the drawings, FIG. 1 shows an example of a "big data" architecture, data architecture 100, demonstrating how data may flow into and throughout a network. In general, a big data system can handle large volumes of data (e.g., terabytes or petabytes of data), receive data and transmit data at high velocities (e.g., near real-time or real-time), and process a large variety of data, such as data having different structure (e.g., structured, semi-structured, unstructured, etc.), data of different types (e.g., text, audio, video, etc.), data associated with different data stores (e.g., relational databases, key-value stores, document databases, graph databases, column-family databases, data analytic stores, search engine databases, time series databases, object store, file systems, etc.), data originating from different sources (e.g., enterprise systems, social networks, clickstreams, Internet of Things (IoT) devices, etc.), data having different rates of change (e.g., batch, streaming, etc.), or data having other heterogeneous characteristics.

Data architecture 100 shows one approach for conceptualizing heterogenous data and how a network may collect, process, store, and utilize the data. One of ordinary skill in the art will appreciate that other embodiments may conceptualize heterogeneous data along different dimensions (e.g., data type, type of data store, source, processing rate, etc.) and utilize alternative processing frameworks without departing from the scope of the present disclosure. In this example, data architecture 100 includes data source layer 102, data collection layer 120, data storage layer 140, data analytics layer 160, data governance tier 170, metadata management tier 180, and security management tier 190. For any system or system element discussed herein, there can be additional, fewer, or alternative components arranged in similar or alternative orders, or in parallel, within the scope of the various embodiments unless otherwise stated.

Data source layer 102 can include structured data 104, semi-structured data 106, and unstructured data 108. Structured data 104 is a type of data neatly arranged by delimiters or other formatting elements so that a computer can understand its structure. Structured data 104 can represent data entities that have a well-defined format and follow a predefined schema. Another aspect characterizing structured data 104 is that it may comprise a set of attributes having specific data types and/or other constraints such that data collection layer 120 can pre-allocate memory/storage upon ingestion (e.g., schema on write). Some examples of structured data 104 include data from enterprise systems and mainframes (e.g., accounting, billing, business intelligence, configuration management (CM), customer relationship management (CRM), enterprise asset management (EAM), enterprise resource planning (ERP), file system, supply chain management (SCM), etc.), online transactions processing (OLTP) systems, flat delimited files (e.g., comma-separated values (CSV)), and the like.

Semi-structured data 106 is similar to structured data 104 but may include fewer structural constraints. For instance, semi-structured data 106 can be loosely coupled to a schema and use the schema as general guidance for the structure of its data. However, the schema in semi-structured data 106 can vary from record to record. In some cases, semi-structured data 106 express complex relationships between data entities that cannot be intuitively represented using relational databases (e.g., records having random multi-nested fields, missing fields, different fields, similar fields associated with different data types, etc.). Examples of semi-structured data 106 can include data stored or exchanged in formats such as Javascript Notation (JSON), Resource Description Framework (RDF), extensible mark-up language (XML), or other suitable standards or definitions; log data; or clickstream data; among other possibilities.

Unstructured data 108 generally includes information that may not conform to a particular structure or data model. Unstructured data 108 is often haphazardly organized such that it may be difficult for a computer to parse or separate into fields consistently found in each record of the data. Some examples of unstructured data 108 include the content of e-mails, Short Message Service (SMS) texts, instant messenger messages or chat transcripts, social network data, collaboration data, speech-to-text transcripts, video conference files, audio files, voicemails, and other electronic communications; word processing documents, spreadsheets, presentations, and other office documents; machine-generated data, such as Radio-frequency identification (RFID) data, Internet of Things (IoT) data, instrumentation/sensor data, event logs, file system information, configuration data, UNIX®/LINUX® data (e.g., output of PS, IOSTAT, and TOP utilities) and similar machine status data, virtualization data (e.g., hypervisor, guest operating system, virtual machine, container data, etc.), cloud data (e.g., provisioned computing, memory, storage, and network instance data), network telemetry (e.g., network flow data, web visitor logs,), or other information generated by machines; images, audio files, videos, or other media and multimedia files; or any other machine-readable data whose contents may not adhere to a particular format.

Data collection layer 120 may include extract, transform, and load (ETL) processing framework 122 batch processing framework 124, and stream processing framework 126. ETL processing framework 122 can include enterprise systems for extracting (primarily structured) data, transforming the extracted data for storage in the proper format, and loading the transformed data into a target ETL data sink in data storage layer 140. The ETL data sink may include enterprise data warehouse (142), data marts (e.g., a data store representing a subset of the data of EDW 142), operational data stores (ODS) (e.g., a data store whose contents comprise additionally processed data from a subset of EDW 142, enterprise data management (EDM) or master data management (MDM) systems (e.g., Teradata®, Talend®, SAS®, etc.), etc). In some embodiments, data collection layer 120 may not include ETL processing framework 122. Instead, data collection layer 120 can integrate ingestion of enterprise system data, such as by having stream processing framework 126 (e.g., Apache Rink®, Apache Samza™, Apache Spark™ Streaming, Apache Storm™, etc.) collect near real-time or real-time data (e.g., data received at a rate exceeding a minimum latency threshold) and batch processing framework 124 (e.g., Apache Hadoop® MapReduce) processing other enterprise system data. In still other embodiments, data collection layer 120 may not segregate data as batch data or streaming data. Instead, data collection layer may use a unified distributive processing framework for inputting all or substantially all data from data source layer 102 (e.g., a massively parallel processing (MPP) framework, a MapReduce framework, a Spark™ framework, etc.).

An MPP framework coordinates processing of an application using multiple processors (e.g., upwards of 200 or more) that work on different portions of the application. Each processor may use its own operating system and memory (e.g., share-nothing). MPP processors can communicate with one another using a messaging interface in an "interconnect" configuration of data paths.

The MapReduce framework is a scalable fault-tolerant system for processing large datasets across a cluster of commodity servers. The MapReduce framework includes a cluster manager (e.g., Apache Hadoop® Yet Another Resource Negotiator (YARN)), a distributed file system (e.g., HDFS™), and a distributed compute engine (e.g., MapReduce).

YARN is a cluster management framework that includes a cluster manager (one per cluster), one or more ApplicationMaster(s) (one per application that can span across several nodes of the cluster) that provide job scheduling and monitoring functionality for each application, and one or more containers per node. The YARN cluster manager comprises a NodeManager (one per node) that operates as a slave for managing the processing resources of a cluster and a ResourceManager (one per cluster) that operates as a master for managing the NodeManager slaves. The ResourceManager includes an ApplicationsManager for accepting jobs from a client application and assigning the first container for running the ApplicationMaster. The Scheduler allocates cluster resources to the ApplicationMaster for running jobs.

The NodeManager manages the resources available on a single node. It reports these resources to the ResourceManager. The ResourceManager manages resources available across the nodes in the cluster, pools together the resources reported by the NodeManagers, and allocates the resources to different applications.

The ApplicationMaster is generally provided by a distributive processing framework (e.g., Spark™, MapReduce, etc.). The ApplicationMaster owns and executes a job on a YARN cluster, negotiates resources with the ResourceManager, and works with the NodeManagers to execute a job using containers. The ApplicationMaster also monitors jobs and tracks progress. Containers represent the resources available to an application on a single node. The ApplicationMaster obtains the containers required to execute a job with the ResourceManager. On successful allocation, the ApplicationMaster launches containers on the cluster nodes working with the NodeManagers.

HDFS™ is a distributed file system that stores data across a cluster of commodity servers (e.g., general-purpose computers that are standardized, readily available, and easily replaceable). In some embodiments, HDFS™ utilizes block storage or fixed-size blocks (e.g., 128 MB) spread across several different machines in order to parallelize read and write operations performed on data items. Distributing a file to multiple machines increases the risk of a file becoming unavailable if one of the machines in a cluster fails. HDFS™ can mitigate this risk by replicating each file block on multiple machines (e.g., by a replication factor is 3). Thus, if one or two machines serving a file block fail, that file can still be read. An HDFS™® cluster generally includes two types of nodes: a NameNode for managing the file system namespace file metadata, such as file name, permissions, and file block locations) and one or more DataNodes for storing the contents of the file in blocks. To provide fast access to the metadata, the NameNode can store all the metadata in memory.

The NameNode periodically receives two types of messages from the DataNodes in an HDFS™ cluster. One is called Heartbeat and the other is called Blockreport. A DataNode sends a heartbeat message to inform the NameNode that it is functioning properly. A Blockreport contains a list of all the data blocks on a DataNode. When a client application wants to read a file, it first contacts a NameNode. The NameNode responds with the locations of all the blocks that comprise that file. A block location identifies the DataNode that holds data for that file block. A client then directly sends a read request to the DataNodes for each file block.

Similarly, when a client application wants to write data to an HDFS™ file, it first contacts the NameNode and asks it to create a new entry in the HDFS™ namespace. The NameNode checks whether a file with the same name already exists and whether the client has permissions to create a new file. Next, the client application asks the NameNode to choose DataNodes for the first block of the file. It creates a pipeline between all the replica nodes hosting that block and sends the data block to the first DataNode in the pipeline. The first DataNode stores the data block locally and forwards it to the second DataNode, which stores it locally and forwards it to the third DataNode. After the first file block has been stored on all the assigned DataNodes, the client asks the NameNode to select the DataNodes to host replicas of the second block. This process continues until all the file blocks have been stored on the DataNodes. Finally, the client informs the NameNode that the file writing is complete.

MapReduce provides a framework for processing large datasets in parallel across a computer cluster. MapReduce abstracts cluster computing and provides higher-level constructs for writing distributed data processing applications. The MapReduce framework automatically schedules an application's execution across a set of machines in a cluster. MapReduce can handle load balancing, node failures, and complex internode communication.

A MapReduce application includes two functions: map and reduce. Both primitives are borrowed from functional programming. The map function takes a key-value pair as input and outputs a set of intermediate key-value pairs. The MapReduce framework calls the map function once for each key-value pair in the input dataset. Next, it sorts the output from the map functions and groups all intermediate values associated with the same intermediate key. It then passes them as input to the reduce function. The reduce function aggregates those values and outputs the aggregated value along with the intermediate key that it received as its input.

Data storage layer 140 can include EDW 142 and data lake 144. As discussed, this is but one implementation of a data storage layer and other embodiments may include a greater number of elements, fewer elements, or alternative elements. EDW 142 is a centralized, enterprise-wide repository comprising historical and current data from enterprise systems. An enterprise data warehouse is typically used by business intelligence systems to run various analytical queries, and EDW 142 can interface with an OLAP system support multi-dimensional analytical queries.

In some embodiments, data storage layer 140 can also include optimized databases (sometimes referred to as analytical or operational databases) derived from EDW 142 to handle specific reporting and data analysis tasks. Some embodiments may also utilize data marts, subsets of the data stored in EDW 142 that belong to a department, division, or specific line of business of the enterprise. These data stores may be used when the data stored in EDW 142 reaches a size such that average query response times for data analysis tasks exceed a maximum latency threshold.

Data lake 144 is a large data storage repository that holds a vast amount (e.g., substantially all or all of the data flowing through the enterprise) in its native format until it is needed. Data lake 144 is polymorphous and can include various types of databases or data stores, such as relational databases, key-value stores, document databases, graph databases, column-family databases, object store, file systems, etc. Data lake 144 can store data having various structures, including structured data, semi-structured data, and unstructured data. Data lake 144 can also store data in separate physical locations, such as on-premises (e.g., on enterprise-owned or leased property) or off-premises (e.g., within a public cloud) or in memory, disk, tape, or other suitable medium. Although data storage layer 140 includes EDW 142 and data lake 144 as separate, complementary storage systems in this example, other embodiments may implement a data lake that incorporates an enterprise data warehouse.

Data analytics layer 160 can include ad-hoc querying tools 162, reporting tools 164, machine learning/analytics tools 166, and alerting tools 168. Ad-hoc querying tools 162 can provide various interfaces for clients (e.g., end users, applications, etc.) to access data from data storage layer 140, such as through structured query language (SQL) querying engines (e.g., Apache Impala®, Apache Hive™, Presto, etc.), querying APIs of NoSQL databases (e.g., Apache Cassandra®, Apache HBase®, MongoDB®, etc.), text querying of search engines for document data stores (e.g., Apache Solr®, Elasticsearch®, etc.), EDM or MDM systems, and other suitable tools for accessing data from data storage layer 140.

Reporting tools 164 may provide different ways for presenting the data from data storage layer 140, and can include applications that organize and present data as tables; histograms; scatter plots; line, bar, pie, surface, area, flow, and bubble charts; data series or combinations of charts; timelines; Venn diagrams, data flow diagrams, entity relationship (ER) diagrams; word/text/tag clouds, network diagrams, parallel coordinates (e.g., plots of individual data elements across many dimensions); tree maps (e.g., the display of hierarchical data in the form of nested or layered rectangles); cone trees (e.g., the display of hierarchical data in three dimensions in which branches grow in the form of cones); semantic networks (e.g., graphical representations of logical relationships between concepts); dashboards or other interactive visualization software (e.g., Data-Driven Documents (D3) (sometimes also referred to as D3.js), Qlikview®, Tableau®, etc.).

Machine learning/analytics tools 166 can include processes for quantitative analysis, qualitative analysis, data mining, statistical analysis, machine learning, semantic analysis, or visual analysis, among other types of analyses. Quantitative analysis is a data analysis technique that focuses on quantifying the patterns and correlations found in the data. Based on statistical practices, this technique involves analyzing a large number of observations from a dataset. Since the sample size is large, the results can be applied in a generalized manner to the entire dataset.

Qualitative analysis is a data analysis technique that focuses on describing various data qualities using words. It involves analyzing a smaller sample in greater depth compared to quantitative data analysis. These analysis results cannot be generalized to an entire dataset due to the small sample size. They also cannot be measured numerically or used for numerical comparisons. The output of qualitative analysis is a description of the relationship(s) between datasets.

Data mining, also known as data discovery, is a specialized form of data analysis that targets large datasets. Data mining generally refers to automated, software-based techniques that sift through massive datasets to identify patterns and trends. For example, data mining can involve extracting hidden or unknown patterns in the data with the intention of identifying previously unknown patterns. Data mining can form the basis for predictive analytics and business intelligence (BI).

Statistical analysis uses statistical methods based on mathematical formulas as a means for analyzing data. Statistical analysis is often quantitative, but can also be qualitative. This type of analysis is commonly used to describe datasets via summarization, such as providing the mean, median, or mode of statistics associated with the dataset. Statistical analysis can also be used to infer patterns and relationships within the dataset, such as a/b testing (e.g., comparing two versions of an element to determine which is superior based on a pre-defined metric), regression (e.g., determining how a dependent variable is related to an independent variable within a dataset), and correlation (e.g., determining whether two variables are related to each other), among others.

Machine learning takes advantage of the ability of computers to process large amounts of data very quickly to find patterns and relationships with data. Some examples of machine learning techniques include classification, clustering, anomaly detection, or filtering. Classification generally includes two phases, a training phase in which a computer receives training data that is already categorized or labeled so that the computer can develop an understanding of the different categories, and a testing phase, in which the computer applies the knowledge learned during the training phase to classify or label new data.

Clustering is a machine learning technique in which data is divided into different groups so that the data in each group has similar properties. There is no prior learning of categories required. Instead, categories are implicitly generated based on the data groupings. How the data is grouped can depend on the type of algorithm used as each clustering algorithm uses a different technique to identify clusters.

Anomaly detection is the process of finding data that is significantly different from or inconsistent with the rest of the data within a given dataset. This machine learning technique is used to identify outliers, abnormalities, and deviations within a dataset. Some applications of anomaly detection include malicious network activity, fraud detection, medical diagnosis, sensor data analysis, and the like.

Filtering is the automated process of finding relevant items from a pool of items. Items can be filtered either based on a user's own behavior or by matching the behavior of multiple users. Filtering can be collaborative, in which the attributes of a target entity are used to identity other entities having similar attributes and predicting the target entity will behave in a manner similar to those other entities, or content-based, in which the relationship between a first entity and a second entity is identified and used to predict that the first entity will have a similar relationship to a third entity because of the similarities between the second and third entities.

Semantic analysis involves extracting meaningful information from text and speech data. Some applications of semantic analysis include natural language processing, text analytics, or sentiment analysis. Natural language processing algorithms attempt to program a machine to understand speech or text in a similar manner as persons understand the speech or text. Text analytics is the specialized analysis of text through the application of data mining, machine learning, and natural language processing techniques to extract value out of unstructured text. Text analytics can include a parsing phase, in which text is parsed to identify named entities (e.g., proper nouns), pattern-based entities (e.g., telephone number, address, driver's license number, etc.), concepts (e.g., an abstract representation of an entity or group of entities), or relationships between entities, and a categorization phase, in which the text is categorized using the extracted entities, concepts, and relationships between entities. Sentiment analysis is a specialized form of text analysis that focuses on determining the bias or emotions of individuals. This form of analysis determines the attitude of the author of the text by analyzing the text within the context of the natural language.

Visual analysis is a form of data analysis related to the graphic representation of data to enable or enhance its visual perception. The graphic representations of data items can be used to develop a deeper understanding of the data items, such as by identifying and highlighting hidden patterns, correlations, and anomalies. Some examples of visual analysis techniques include heat maps, time series plots, histograms, graphs, and spatial data mapping, among other possibilities.

Alerting tools 168 enable administrators to receive advance notice of events occurring in data architecture 100. In some embodiments, alerting tools 168 can include an interface for the administrators to define rules or trigger conditions that automatically send notifications upon occurrence of the conditions. Some example use cases for alerting tools 168 include login analysis, brute force attack detection, denial of service (DOS) or distributed denial of service (DDOS) attack detection, and the like.

In this example, data architecture 100 includes certain tiers for providing common functionality across data source layer 102, data collection layer 120, data storage layer 140, and data analytics layer 160. An underlying goal of modern enterprise data architectures is to capture substantially all or all of the data passing through the enterprise to analyze the data and to discover insights about the enterprise's business that are not readily apparent to users or not specifically monitored by users. However, the value of data tends to decrease and the risks associated with massive scale storage increase over time. Users can promulgate the rules governing the types of data that data architecture 100 can store. Users can also define the policies for classifying which data is valuable, how long to store the data, and where to store the data at different periods of time. Data governance tier 170 can include tools that downgrade, archive, or delete data based on the classified policy.

Metadata management tier 180 may include functionality for capturing information associated with data items of data architecture 100 (e.g., data other than the content of the data items) across data source layer 102, data collection layer 120, data storage layer 140, and data analytics layer 160. This metadata can include identification information, entity and attribute information, quality information, data lineage, distribution information, and other associated information. In some embodiments, metadata management tier 180 can include indexers for generating indices to enable efficient search of the data items and annotators or decorators for tagging or enhancing the data items with supplemental associated information.

In some embodiments, metadata management tier 180 can support data versioning. For example, administrators can define the structure of raw data of data source layer 102 and describe the entities inside data items of the raw data within metadata management tier 180 (e.g., base-level descriptions). The schemas, ontologies, data models, and the like of data architecture 100 can change over time from interactions between and among data source layer 102, data collection layer 120, data storage layer 140, and data analytics layer 160. Metadata management tier 180 can include versioning tools to monitor the evolution of the schemas, ontologies, and data models.

In some embodiments, components of data analytics layer 160 can interface with metadata management tier 180 to retrieve information that the components need to perform their analytical tasks. Some of the functionality of data analytics layer 160 that metadata management tier 180 can support include self-service business intelligence, (SSBI) data as a service (DaaS), machine learning as a service (MLaaS), data provisioning (DP), analytics sandbox provisioning (ASP), among other services.

Security management tier 190 generally includes functionality for controlling the rights to access, define, and modify data. Security management tier 190 may include tools for managing the creation, usage, and tracking of data across the layers of data architecture 100 and coordinating these rights with security rules. These rules can determine appropriate access control and authentication for data, such as on a need-to-know basis or available to the general public for dissemination. Security management tier 190 can safeguard the appropriate provisioning of data and put suitable security measures in place. For example, if a data set includes an enterprise's transaction and historical data, such as internally sourced customer, product, and/or finance data, as well as data from third-party sources, security management tier 190 can ensure that each of the scopes of the data has the applicable level of security.

Figure 2:
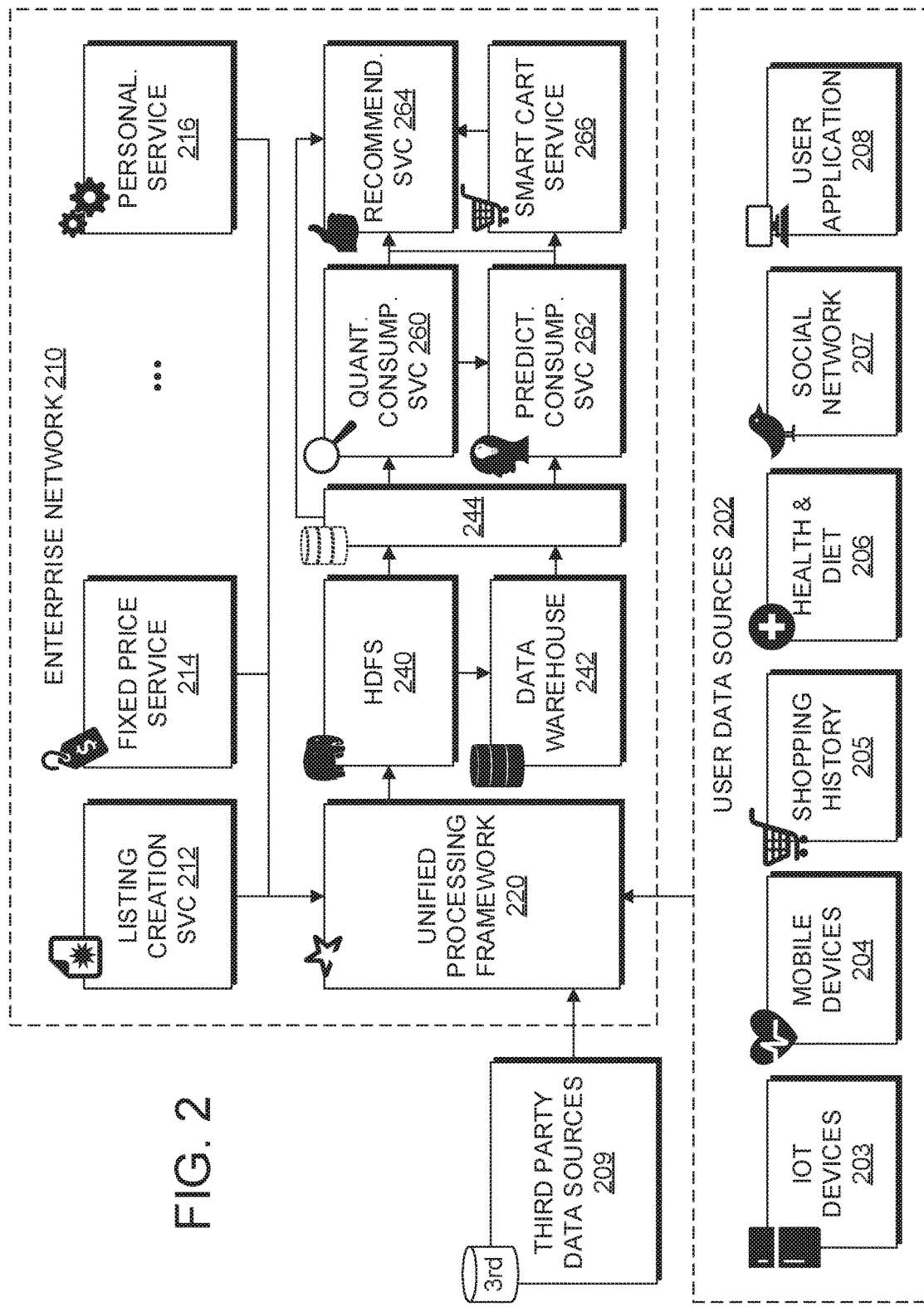
FIG. 2 illustrates an example of a big data system for providing smart virtual shopping cart functionality in accordance with an embodiment.

FIG. 2 shows another example of a big data system, data architecture 200, including elements for supporting smart virtual shopping cart functionality. One of ordinary skill in the art will understand that other embodiments may include additional elements, fewer elements, or different elements without departing from the scope of the present disclosure. For example, other embodiments may implement a data architecture similar to data architectures 100 or 200 but interchange respective elements of these architectures, add elements to these architectures from other data architectures, exclude elements from these data architectures, or exchange elements of these data architectures with elements from other data architectures, and continue to practice the subject matter of the present disclosure.

In this example, data architecture 200 includes user data sources 202, third-party data sources 209, and network 210. For illustrative purposes, network 210 may include online marketplace functionality to enable sellers to create, edit, publish, and otherwise manage listings for items and buyers to search and review item listings, add the item listings to a virtual shopping cart, provide feedback regarding the items or the sellers, and pay for the items. However, a person having ordinary skill in the art will appreciate that data architecture 200 is suitable for other network services or applications, such as content management systems, search engines/web portals, social or user content-sharing networks (e.g., web logs ("blogs"), photos, videos, etc.), forum/question-and-answer websites, news websites, online encyclopedias, media streaming networks (e.g., music, videos, multimedia, etc.), content aggregators, product review sites, corporate sites, personal sites, file-sharing sites, among others.

In this example, user data sources 202 include Internet of Things (IoT) device data 203, mobile device data 204, shopping history data 205, health and diet data 206, social network data 207, and user application data 208. In other embodiments, user data sources 202 may include any other personal user data that users have authorized network 210 to receive. IoT device data 203 may include data captured by sensors and devices that are generally fixed about users' homes, offices, and other frequented locations that provide information relating to users' health, diet, fitness, and the like. Some examples of IoT device data 203 include data captured by "smart" refrigerators, stoves, microwaves, or other kitchen appliances; "smart" digital thermometers, beverage containers, or smart kitchen utensils, tools, and containers; "smart" trash cans; "smart" kitchen scales for measuring ingredients; "smart" digital scales for measuring user weight; "smart" universal product code (UPC), Quick Response® code, or other machine-readable code readers or other inventory-tracking devices; "smart" cameras; and other "smart" home devices.

Mobile device data 204 can include data from sensors and I/O components of portable electronic devices (e.g., smartphones, tablets, wearable devices, etc.) that can be carried by users or that can be affixed to users' bodies to provide information relating to the users' health, diet, fitness, and the like. Some examples of mobile device data 204 include data from global positioning systems (GPS), accelerometers, gyroscopes, magnetometers, inclinometers, proximity sensors, distance sensors, depth sensors, range finders, ultrasonic transceivers, or other motion/position/orientation sensors and devices; cameras, ambient light sensors, infrared (IR) transceivers, ultraviolet (UV) transceivers, or other optical, light, imaging, or photon sensors; heart rate, respiratory rate, blood pressure, body temperature, myocardial, electrocardiogram (ECG), electroencephalogram (EEG) sensors, blood oxygen sensors; food intake monitors (e.g., acoustic, image processing, inertial, electroglottography (EGG), electromyography (EMG), piezoelectric, proximity, and respiratory inductance plethysmography devices and sensors for detecting biting, chewing, or swallowing); ingestible sensors (e.g., sensors the size of pills that users can swallow for each meal); or other biometric sensors.

Shopping history data 205 may include data sources external to network 210 that provide information relating to users' purchases of items, such as groceries, food items, or other items that correlate to users' health, diet, fitness, and the like. For example, a user's purchase of tickets to a football game, charcoal, and lighter fluid may indicate that the user has an interest in hamburgers and hot dogs for a tailgate party, or purchases of a New Orleans cookbook and a ten-gallon pot may indicate that the user has an interest in Cajun food and ingredients. Users may link their users accounts with network 210 to their user accounts with other network services or applications, or otherwise share with network 210 their shopping histories from other online marketplaces, online restaurant or food delivery services, online grocery or ingredient-and-recipe meal kit services, grocery store loyalty programs or other loyalty programs of other e-commerce services and applications from whom users have purchased food items.

Health and diet data 206 can include information from physicians, physical therapists, dieticians, or other health care providers that users have consented to share or have directly shared with network 210 relating to the user's health, diet, fitness, and the like (e.g., open Electronic Health Records (openEHR), Fast Healthcare Interoperability Resources (FHIR), Clinical Document Architecture (CDA) files, and other EHRs). Health and diet data 206 can also include food allergy information, dietary restrictions, prescribed diet and exercise plans, and the like. In some embodiments, health and diet data 206 may include information from users' physical trainers or other fitness consultants relating to exercise regimens, information from exercise equipment relating to exercises performed, and similar fitness and exercise data.

Social network data 207 may include information relating to users' social network interactions, and can include shared photos, videos, events, web log (blog) entries, social network posts, hyperlinks, and other shared content; demographic information (e.g., gender, age, race/ethnicity, geographic region history, education history, work history, relationship history, relationships, etc.); status information (e.g., current geolocation, activity, mood, etc.); personal preferences (e.g., favorite films, books, music, etc.); contacts, group memberships, and other user affinity or affiliation information; "likes," "dislikes," ratings, comments, and other sentiment information; and other online social activities.

User application data 208 can include information relating to health, diet, fitness, and the like that users enter into third party applications e.g., diet and exercise journals; spreadsheets or comma-separated value (CSV) files; etc. or that are otherwise captured by the third-party applications. In some embodiments, users may provide user application data 208 to network 210 through application programming interfaces (APIs) (e.g., restful state transfer (REST), Simple Object Access Protocol (SOAP), Service Oriented Architecture (SOA), etc.) provided by the user applications and/or network 210.

Third-party data sources 209 can include data stores unassociated with user data sources 202 and external to network 210 that relate to user health, diet, fitness, and the like. Some examples of third party data sources 209 include nutritional databases the United States Department of Agriculture (USDA) Food Composition Databases), product databases (e.g., Open Product Data), recipe databases (e.g., Fork the Cookbook), restaurant recipe/nutritional databases (e.g., Nutritionix®), foodborne outbreak tracking systems (e.g., the Foodborne Outbreak Online Database (FOOD) Tool from the Center for Disease Control and Prevention (CDC)), among others.

Network 210 may communicate with user data sources 202 or third-party data sources 209 over APIs provided by network 210 (e.g., if user data sources 202 or third-party data sources 209 "pushes" the data to network 210) or user data sources 202 or third-party data sources 209 (e.g., if network 210 "pulls" the data from user data sources 202 or third-party data sources 209). In some embodiments, the APIs may follow a restful state transfer (REST) design pattern in which the server computing system enables the client computing system to access and interact with resources via uniform resource identifiers (URIs) using a set of predefined stateless operations (referred to as endpoints). The server and client may exchange requests and responses in JSON or XML format.

An example of third-party data source 209 is the National Nutrient Database (NDB) provided by the USDA. The USDA offers several REST API endpoints to obtain nutritional data for food items. Table 1A provides an example of request parameters of an NDB REST API endpoint for a nutrient report, and Table 1B provides an example of an invocation of the NDB REST API endpoint.

TABLE 1A

Example request parameters for USDA NDB REST API endpoint

| Parameter | Required | Default | Description |
|---|---|---|---|
| api_key | y | n/a | A data.gov registered API key |
| fg | n | " " | Food group |
| format | n | JSON | Output format e.g., XML or JSON) |
| max | n | 50 | Number of rows to return (maximum per request is 1,500) |
| offset | n | 0 | Beginning row in the result set to begin |
| nbno | n | n/a | Nutrient number (nutrient for a single food identified by its unique id) |
| nutrients | y | n/a | A list of up to a maximum of 20 nutrient_id's to include in the output |
| sort | n | f | Sort the list of foods by (f)ood name or nutrient (c)ontent; if requesting more than one nutrient and specifying sort = c, then the first nutrient in list is used for the content sort |
| Subset | n | 0 | Can request all the foods in the database or an abridged list from the pull down menu; set the subset parameter to 1 for the abridged list of about 1,000 foods commonly consumed in the U.S.; the default is 0 for all of the foods in the database |

TABLE 1B

Example request to USDA NDB REST API endpoint curl -H "Content-Type:application/json" -d
'{"nutrients":["204","205","208","269"],"max":25,"offset":0}'
DEMO_KEY@api.nal.usda.gov/ndb/nutrients Table 2A provides an example of the response parameters of the USDA NDB REST API endpoint, Table 2B provides an example of a snippet of the response, and Table 2C provides a tabular view of the snippet of the response.

TABLE 2A

Example response parameters of USDA NDB REST API endpoint

| Report | Basic information about the report |
|---|---|
| group | If applicable; the list of food groups used to filter the report |
| subset | The name of the subset of foods in the response or all foods |
| sr | Standard Release version of the output data being reported |
| end | The number of the last item in the output -- normally start + max |
| start | Value of the offset parameter used in the output |
| total | The total number of items available in the output; useful for paging the report |
| Foods | A list of foods |
| ndbno | Nutritional database food number |
| name | Food name |
| measure | Household measure represented by the nutrient value element |
| nutrients | List of nutrients and their values for a food |
| nutrient_id | Nutrient Number |
| nutrient | Description of the nutrient |
| unit | Unit in which the nutrient value is expressed |
| gm | The 100 gram equivalent value for the nutrient |
| value | Value of the nutrient for this food |

TABLE 2B

Example response of the USDA NBD REST API endpoint

```
{
"report": {
"sr": "28",
"groups": "All groups",
"subset": "All foods",
"end": 150,
```

TABLE 2B-continued

Example response of the USDA NBD REST API endpoint

```
"start": 0,
"total": 8488,
"foods": [
{
"ndbno": "09427",
"name": "Abiyuch, raw",
"weight": 114,
"measure": "0.5 cup",
"nutrients": [
{
"nutrient_id": "208",
"nutrient": "Energy",
"unit": "kcal",
"value": "79",
"gm": 69
},
{
"nutrient_id": "269",
"nutrient": "Sugars, total",
"unit": "g",
"value": "9.75",
"gm": 8.55
},
{
"nutrient_id": "204",
"nutrient": "Total lipid (fat)",
"unit": "g",
"value": "0.11",
"gm": 0.1
},
{
"nutrient_id": "205",
"nutrient": "Carbohydrate, by difference",
"unit": "g",
"value": "20.06",
"gm": 17.6
}
]
},
{
"ndbno": "09002",
"name": "Acerola juice, raw",
"weight": 242,
"measure": "1.0 cup",
"nutrients": [
{
"nutrient_id": "208",
"nutrient": "Energy",
"unit": "kcal",
```

TABLE 2B-continued

Example response of the USDA NBD REST API endpoint

```
"value": "56",
"gm": 23
},
{
"nutrient_id": "269",
"nutrient": "Sugars, total",
"unit": "g",
"value": "10.89",
"gm": 4.5
},
{
"nutrient_id": "204",
"nutrient": "Total lipid (fat)",
"unit": "g",
"value": "0.73",
"gm": 0.3
},
{
"nutrient_id": "205",
"nutrient": "Carbohydrate, by difference",
"unit": "g",
"value": "11.62",
"gm": 4.8
}
]
},
{
"ndbno": "09001",
"name": "Acerola, (west indian cherry), raw",
"weight": 98,
"measure": "1.0 cup",
"nutrients": [
{
"nutrient_id": "208",
"nutrient": "Energy",
"unit": "kcal",
"value": "31",
"gm": 32
},
{
"nutrient_id": "269",
"nutrient": "Sugars, total",
"unit": "g",
"value": "--",
"gm": "--"
},
{
"nutrient_id": "204",
"nutrient": "Total lipid (fat)",
"unit": "g",
"value": "0.29",
"gm": 0.3
},
{
"nutrient_id": "205",
"nutrient": "Carbohydrate, by difference",
"unit": "g",
"value": "7.54",
"gm": 7.69
}
]
}
```

TABLE 2C

Tabular view of example response of USDA NDB REST API endpoint

| report | |
| --- | --- |
| sr | 28 |
| groups | All groups |
| subset | All foods |
| end | 150 |
| start | 0 |
| total foods | 8488 |

| | | | | nutrients | | | | |
| --- | --- | --- | --- | --- | --- | --- | --- | --- |
| ndbno | name | weight | measure | nutrient_id | nutrient | unit | value | gm |
| 09427 | Abiyuch, raw | 114 | 0.5 cup | 208 | Energy | kcal | 79 | 69 |
| | | | | 269 | Sugars, total | g | 9.75 | 8.55 |
| | | | | 204 | Total lipid (fat) | g | 0.11 | 0.1 |
| | | | | 205 | Carbohydrate, by difference | g | 20.06 | 17.6 |
| 09002 | Acerola juice, raw | 242 | 1.0 cup | 208 | Energy | kcal | 56 | 23 |
| | | | | 269 | Sugars, total | g | 10.89 | 4.5 |
| | | | | 204 | Total lipid (fat) | g | 0.73 | 0.3 |
| | | | | 205 | Carbohydrate, by difference | g | 11.62 | 4.8 |
| 09001 | Acerola, (west indian cherry), raw | 98 | 1.0 cup | 208 | Energy | kcal | 31 | 32 |
| | | | | 269 | Sugars, total | g | — | — |
| | | | | 204 | Total lipid (fat) | g | 0.29 | 0.3 |
| | | | | 205 | Carbohydrate, by difference | | | |

In an embodiment, a network may ingest third-party data source 209 all at once and periodically poll the data source for updates or have the data source push updates to the network. By including third-party data source 209 in its own ecosystem, the network can locate the data closer (e.g., geographically and/or fewer network hops) to where applications that consume the data are located. In addition, the network is not dependent on and not limited by the resources of the third-party. In some embodiments, third-party data source 209 may operate as a data mart or other independent or semi-independent data store in the network. In other embodiments, for the network The data sources of data architecture 200 also include information input into and stored by network 210, such as listing creation service 212 for enabling users to list items, fixed price service 214 for enabling buyers to purchase items or add items to a virtual shopping cart, and personalization service 216 for enabling buyers and sellers to configure settings for their accounts with network 210. The services of network 210 are discussed in further detail below.

Data architecture 200 illustrates other dimensions of the heterogeneity of data sources with which a network may have to contend. For example, data sources may be internal (e.g., listing creation service 212, fixed price service 214, personalization service 216, etc.) or external (e.g., user data sources 202 and third-party data sources 209). Data sources may come from a wide variety of devices and origins (e.g., IoT devices 203, mobile devices 204, enterprise systems that provide shopping history data 205, social networks 207, computing devices that provide user application data 208, etc.). These different data sources implicitly include data of different types, structures, and rates of transmission. For example, an OLTP system ay provide structured shopping history data 205 at a batch rate, social network data 207 may consist of a stream of semi-structured or unstructured text messages, or a smart security camera may provide IoT device data 203 in the form of unstructured audio/video data at burst rates when the camera detects motion.

Data architecture 200 also illustrates another approach for processing heterogeneous data—using a unified distributive data processing framework for collecting, processing, and storing the data. Such an approach can have certain have advantages. For example, all downstream components of the data pipeline can benefit from improvements in the upstream component. Thus, when the upstream component is optimized, all downstream components gain the improvements as well. Another potential benefit with a unified processing framework is the reduction of resources associated with deploying and maintaining fewer independent software systems. In addition, each time a new component is added to the upstream component, it can be immediately available to all downstream components. Implementing a new type of data analysis can become a matter of invoking the new component rather than designing new systems for each processing framework. Finally, one of the largest advantages of tight integration is the ability to build applications that seamlessly combine different processing models. For example, a group of developers can write an application that uses machine learning to classify data in real time as it is ingested from streaming sources. Simultaneously, a group of data analysts can query the resulting data in real time using SQL (e.g., to join the data with unstructured logfiles) and another group of data engineers and data scientists can access the same data via shell for ad-hoc analysis. Yet another group might access the data in standalone batch applications. All the while, an operations team can maintain one system for all of these concurrent activities.

In this example, data architecture 200 implements unified processing framework 220 using Apache Spark™ 2.x+. Spark™ is an in-memory cluster computing framework for processing and analyzing large datasets and a wide range of workloads (e.g., batch, iterative, interactive, streaming, etc.). The Spark™ framework comprises Spark™ Core, Spark™ SQL, Spark™ Streaming, MLib, and GraphX.

Spark™ Core provides the basic functionality of the Spark™ processing framework, and includes components for task scheduling, memory management, fault recovery, and interacting with storage systems, among others. Spark™ Core also includes the API for the Spark™ framework's basic building blocks, resilient distributed datasets (RDDs). RDDs represent a collection of items distributed across many compute nodes that can be operated upon in parallel. Spark™ Core provides the functions for operating on these collections.

Spark™ SQL is a component of the Spark™ framework that allows for querying of data persisted in a variety of types of data stores (e.g., key-value stores, graph databases, column-family databases, etc.) using SQL or variants (e.g., Apache Hive™ Query Language (HQL)). Spark™ SQL also supports integration of SQL and SQL-like queries with operations on RDDs using programmatic languages Python™, Oracle Java®, Scala, etc.

Spark™ Streaming is a component of the Spark™ framework for processing data streams. Spark™ Streaming provides an API for operating on data streams that closely matches Spark™ Core's API for operating on RDDs, making it easy for programmers to learn the project and move between applications that manipulate data stored in memory, on disk, or arriving in real time.

MLlib is a machine learning library, and provides functionality for classification, regression, clustering, and collaborative filtering, as well as supporting functionality such as model evaluation and data import. MLlib also exposes some lower-level ML primitives, such as generic gradient descent optimization.

GraphX is a library for operating on graphs and performing graph computations in parallel. GraphX also provides functions for operating on portions of a graph (e.g., vertices, edges, subgraphs) and common graph algorithms (e.g., PageRank, triangle counting, etc.).

A Spark™ application generally includes a driver program, a cluster manager, workers, executors, and tasks. The driver program operates as a library to provide the data processing code executed by the workers. The cluster manager acquires resources for executing the application. The cluster manager (e.g., standalone, Apache Mesos®, YARN, etc.) coordinates computing resources across a cluster, provides low-level scheduling of cluster resources across applications, and enables multiple applications to share cluster resources and run on the same workers. The workers provide CPU, memory, and storage resources to the application and run the application as distributed processes on a cluster. The executors are virtual machines (e.g., Java® virtual machine (JVM)) created on each worker. The executors can execute code concurrently in multiple threads, and can also cache data in memory or disk. A task is the smallest unit of work the application sends to an executor, which is executed by a thread in the executor. Each task performs some computations to either return a result to the driver program or partition its output for shuffle. The Spark™ application creates a task per data partition. As executors can run one or more tasks concurrently, the amount of parallelism is determined by the number of partitions. More partitions mean more tasks processing data in parallel.

Unified processing framework 220 can collect data from heterogeneous data streams (e.g., user data sources 202, third party data sources 209, data sources/sinks of network services 212, 214, 216, etc.), process the data, and store the data to HDFS™ 240. HDFS™ 240 can effectively operate as an operational data store, and copy data that needs to be persisted to data warehouse 242, and data warehouse 242 can effectively operate as a master data store. Data virtualization layer 244 can operate to abstract away the complexities of the interrelationship between HDFS™ 240 and date warehouse, and provide access to all data sources and to support different modes of access to support analytical services (e.g., quantitative consumption service 260 and predictive consumption service 262) and downstream services (e.g., recommendation service 264 and smart virtual shopping cart service 266).

Quantitative consumption service 260 is an example of a quantitative analytical tool for determining a user's consumption of food within a predetermined time period. Quantitative consumption service 260 can utilize a variety of techniques for its analysis. In some embodiments, quantitative consumption service 260 can apply computer vision/object recognition and machine learning processes (e.g., classification algorithms) to image data associated with the user to determine user consumption. For example, the user may take a photo of every snack and meal to send to network 210 or network 210 can collect image or video data from various user data sources (e.g., mobile device cameras, cameras on smart home devices, IP cameras, photos shared on a social network feed, etc.). Quantitative consumption service 260 may identify food items in the image data and correlate those food items with their associated nutritional data to determine dietary amounts (e.g., calories, nutrients, vitamins, minerals, etc.) consumed by the user.

Alternatively or in addition, quantitative consumption service 260 can analyze shopping history data 205, recipes provided by a smart home speaker, data from a food intake monitor, or other data indicative of user consumption. In some embodiments, quantitative consumption service 260 can present its best estimates of the user's consumption for the user to revise if necessary. The user's behavior with respect to the estimates can operate as additional data points for improving its analysis.

Predictive consumption service 262 is an example of a predictive analytical tool for predicting user consumption based on purchase of a food item. Predictive consumption service 262 can evaluate a specific user's behavior after purchasing the food item (including data captured by quantitative consumption service 260), demographically similar users purchasing the same item, and/or all users purchasing the same item to predict when the user will consume the food item and how much of the food item the user will consume.

Recommendation service 264 is an example of a filtering tool that can provide users with recommended food items to help them achieve their dietary goals. In some embodiments, recommendation service may receive an indication that purchasing a food item may cause the user to fail to meet one of his/her dietary goals, such as receiving this information directly from smart virtual shopping cart service 266 or by evaluating a user's dietary goals, current user consumption data from quantitative consumption service 260, and predicted consumption data associated with purchasing a particular food item from predictive consumption service 262. In such an event, recommendation service 264 can analyze the specific user's shopping history data, demographically similar users' shopping history data, and/or all user's shopping history data to find a substitute food item.

In some embodiments, recommendation service 264 may identify users successfully meeting their dietary goals and their recently purchased food items and recommend those food items to demographically similar users or users attempting to achieve similar goals. In some embodiments, recommendation service 264 may analyze historical trend data and/or current trend data relating to food item purchases to provide recommendations to users. In some embodiments, recommendation service 264 may analyze user rating data for food items and recommend highly rated food items to users. In some embodiments, recommendation service 264 may review a user's dietary goals and dietary preferences to provide recommendations to the user. Other embodiments may use various other recommendation algorithms known to one of ordinary skill subject to the condition that recommended food items should not cause users to fail to meet their dietary goals.

Smart virtual shopping cart service 266 is a downstream network service that evaluates a user's dietary goals, current user consumption data from quantitative consumption service 260, and predicted consumption data associated with a food item from predictive consumption service 262 to determine whether purchase of the food item would cause the user to fail one of his/her dietary goals. In such an event, smart virtual shopping cart service 266 can issue warnings to the user, communicate with recommendation service 264 to provide recommendations for substitute food items, automatically removing the food item from a virtual shopping cart, automatically replacing the food item with a recommended substitute food item FIGS. 3A-3I show examples of graphical user interfaces (within bold lines) for a network including online marketplace functionality (e.g., network 210 of FIG. 2) presented on web browser 302 of a client device (e.g., computing system 800 of FIG. 8). In these examples, web browser 302 is a desktop application, Microsoft Internet Explorer®, pointed to one example of a network including online marketplace functionality, eBay® Inc. Other embodiments may utilize other web browsers for desktop computers or mobile devices (e.g., Google Chrome®, Mozilla Firefox®, Apple Safari®, etc.) or standalone applications (e.g., eBay® mobile app for Google Android®, Apple iOS®, etc.) for presenting graphical user interfaces of the network.

Figure 3A:
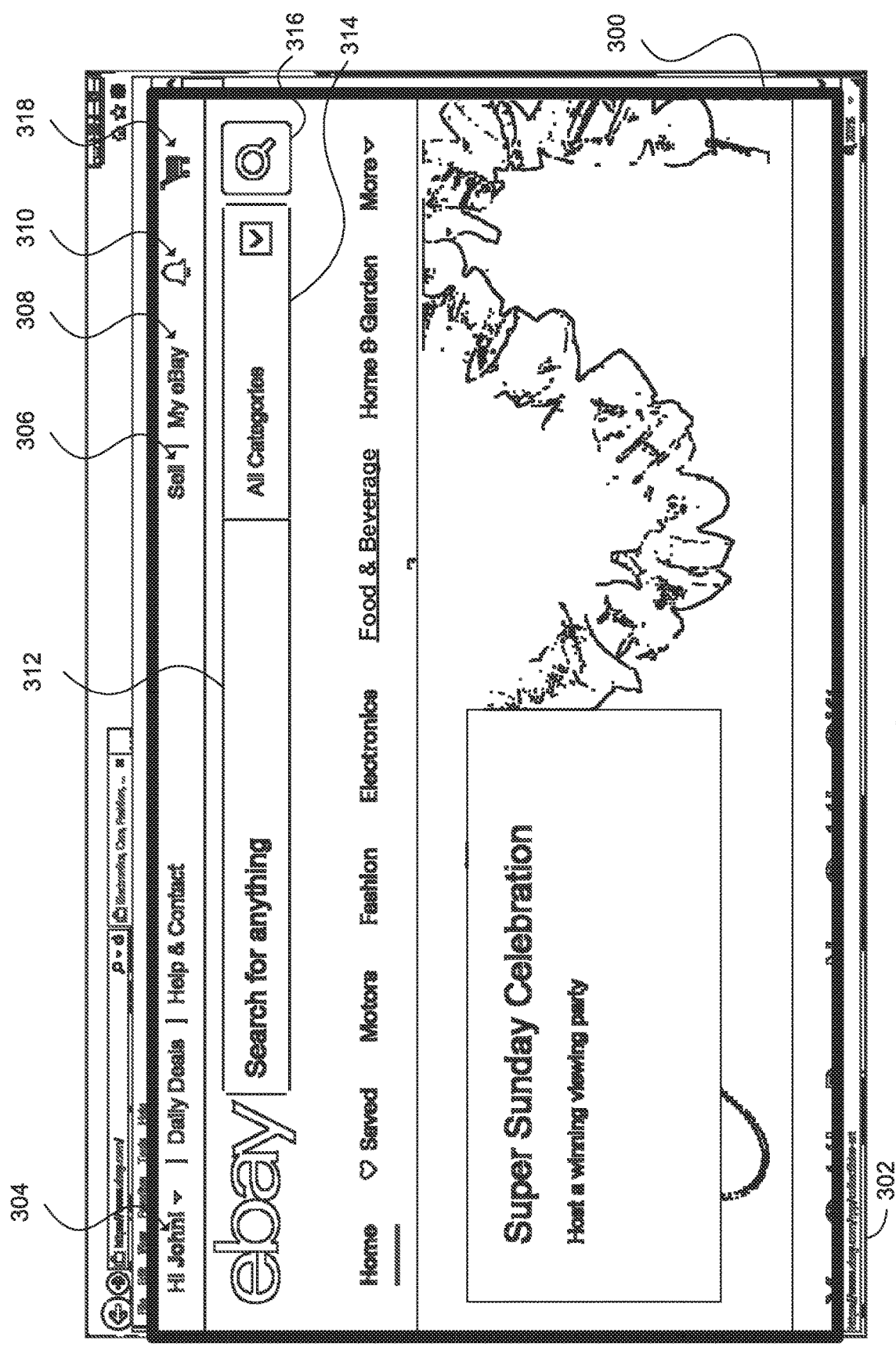

FIG. 3A shows an example of a graphical user interface, homepage 300, presented to a user upon the user initially navigating to the network (e.g., http://www.ebay.com/) via web browser 302. In this example, homepage 300 includes various user interface elements for the user to interact with the network, such as account settings selection element 304, seller user interfaces selection element 306, personalization user interface selection element 308, messaging user interface selection element 310, keyword entry user interface element 312, category user interface selection elements 314, keyword search user interface element 316, and shopping cart user interface selection element 318.

In this example, selection (e.g., clicking on a user interface element via a mouse, touching the user interface element via a touchscreen, voice command, etc.) of account settings selection element 304 can navigate web browser 302 to user interfaces for updating a user's personal information (e.g., user identifier, password, security reminder questions, etc.), the user's shipping and mailing addresses, communication preferences, site preferences, and other settings associated with the user's account with the network. In some embodiments, users can also review and update personal health, diet, and fitness information to help them identify more relevant content and purchase food items that will enable them to achieve their goals.

FIG. 3B shows an example of a graphical user interface, health settings overview 320, that a user of the network may utilize to view and edit personal health, diet, and fitness information. Health settings overview 320 includes a side navigation bar with user health profile user interface selection element 322A, medical information user interface selection element 324A, health, diet, and fitness plan user interface selection element 326A, daily tracker user interface selection element 328A, registered devices user interface selection element 330A, purchasing information user interface selection element 332, dietary preferences user interface selection element 334, recipe information user interface selection element 336, and group information user interface selection element 338.

In this example, health settings overview 320 provides health profile user interface 322B and medical information user interface 322B by default. Health profile user interface 322B can display and enable the user to edit personal information that may be relevant to the user's health, diet, fitness, and the like, such as the user's age, gender, level of activity (e.g., sedentary activity level for little to no exercise; moderate activity level for low-intensity exercise that typically will not cause the user break a sweat, such as an easy walk, stretching, light gardening, etc.; and high activity level for regular exercise for at least one hour and fifteen minutes every week), height, and weight. In some embodiments, the network can automatically identify the user's level of activity from mobile device and wearable device data streams (e.g., heart rate, respiratory rate, blood oxygen, and perspiration levels; GPS readings; accelerometer, gyroscope, magnetometer, and other motion/position/orientation sensor measurements; ECG and EEG waveforms; etc.). In some embodiments, health profile user interface 322B can also display and allow the user to modify body fat percentage, body mass index, lean body mass, waist circumference, and other physical measurements.

Medical information user interface 322B can display and enable a user, other persons (e.g., physicians, nurses, caretakers, etc.), or devices to update the user's medical information, such as blood pressure, blood alcohol content, blood glucose level, total cholesterol level, low-density lipoprotein (LDL) cholesterol or "bad" cholesterol level, high-density lipoprotein (HDL) or "good" cholesterol level, triglycerides. In some embodiments, medical information user interface 322B can also list the user's blood type, food allergies (e.g., milk, egg, peanuts, tree nuts, soy, wheat, fish, shellfish, sesame, etc.), medications, reproductive health information (e.g., basal body temperature, cervical mucus quality, menstruation, etc.), medical conditions, medical health history, family diseases, and other medical information.

Figure 3C:
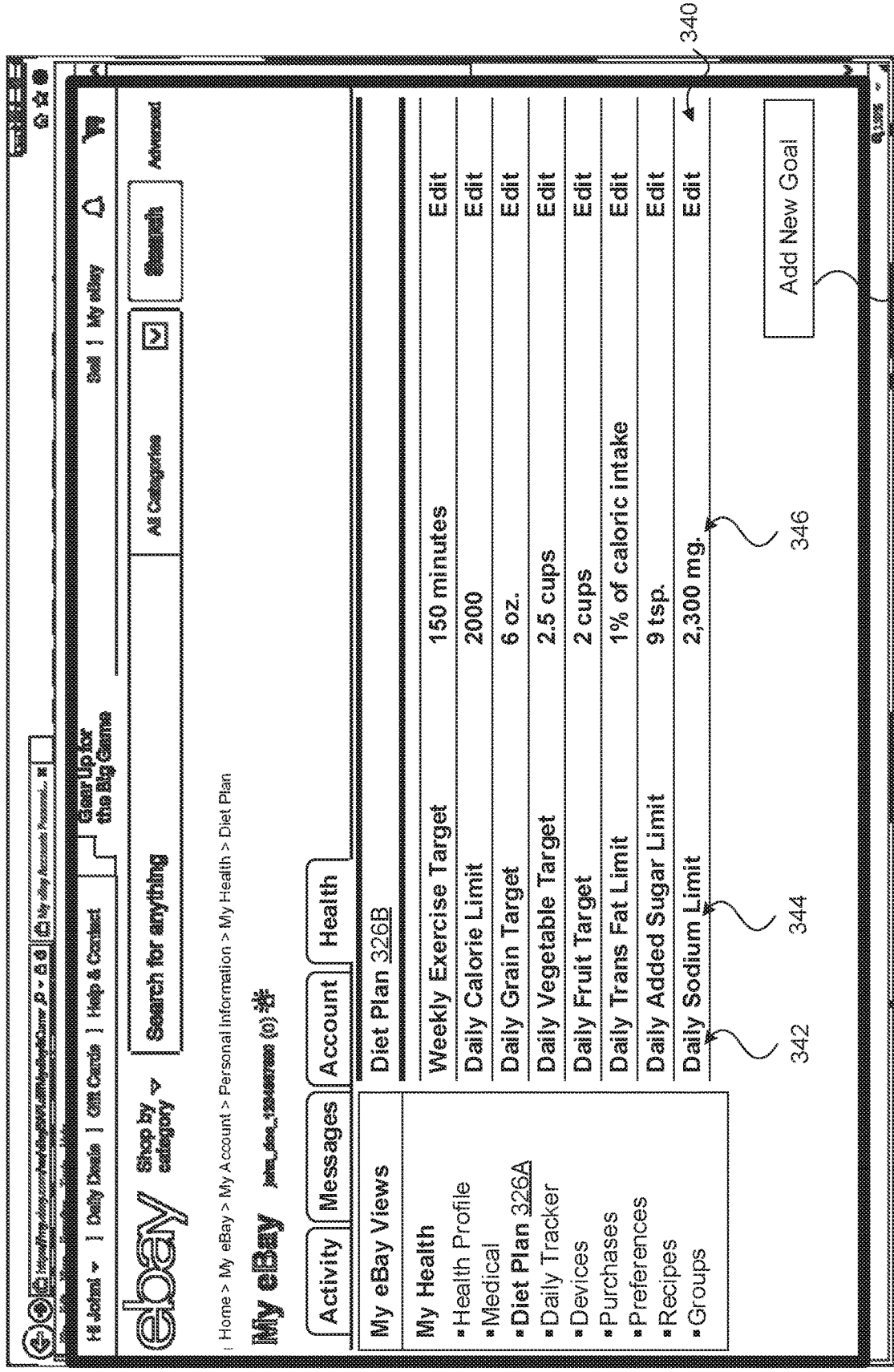

FIG. 3C shows an example of a graphical user interface, health, diet, and fitness plan 326B, which may be presented by web browser 302 upon selection of health, diet, and fitness plan user interface selection element 326A. In this example, each row of health, diet, and fitness plan 326B represents a user's health, diet, or fitness goal or condition 340. Goal or condition 340 can specify time period 342 (e.g., daily, weekly, monthly, seasonal, etc.) by which to achieve the goal or condition, activity 344 (e.g., exercise, consumption of certain amounts of nutrients or types of food, refrain from consuming certain amounts of nutrients or types of food), and quantity 346 (e.g., absolute quantity or relative quantity) associated with the goal or condition. For example, health, diet, and fitness plan 326B includes a target (e.g., a minimum amount to achieve the goal or condition) to exercise at least 150 minutes each week; limits (e.g., maximum amounts not to be exceeded) of 2000 calories, 1% of caloric intake attributable to trans fats, 9 teaspoons of added sugar, and 2,300 mg. of sodium each day; and targets of 6 oz. of grain, 2.5 cups of grains, and 2 cups of fruit each day. In some embodiments, health, diet, and fitness plan 326B can also include avoidance of the user's food allergies as a goal or condition (e.g., a zero limit or other tolerable minimum threshold for an allergen).

In this example, the user can also add new goals or conditions by selecting user interface element 348. In other embodiments, the network may include a diet plan service (e.g., recommendation service 264) that can automatically create user health, diet, and fitness goals or conditions based on user selection of a predetermined diet plan (e.g., Dietary Approaches to Stop Hypertension (DASH) diet, Therapeutic Lifestyle Changes (TLC) diet, the Mayo Clinic® diet, etc.). In still other embodiments, the diet plan service automatically generate a diet plan by evaluating professional medical advice; dietary guidelines from the USDA, Health and Human Services (HHS), or other governmental bodies; historical user information of other users having the same or similar demographic traits as the user; or a combination of these approaches (e.g., average of two or more dietary goals or conditions, median of the dietary goals or conditions from each approach, weighted combination of the dietary goals or conditions, a machine learning process that extracts a dietary goal or condition from each approach as a feature and selects the best set of features/dietary goals or conditions to achieve the user's selected outcome (e.g., weight loss, reducing hypertension, increasing energy, etc.)).

Figure 3D:
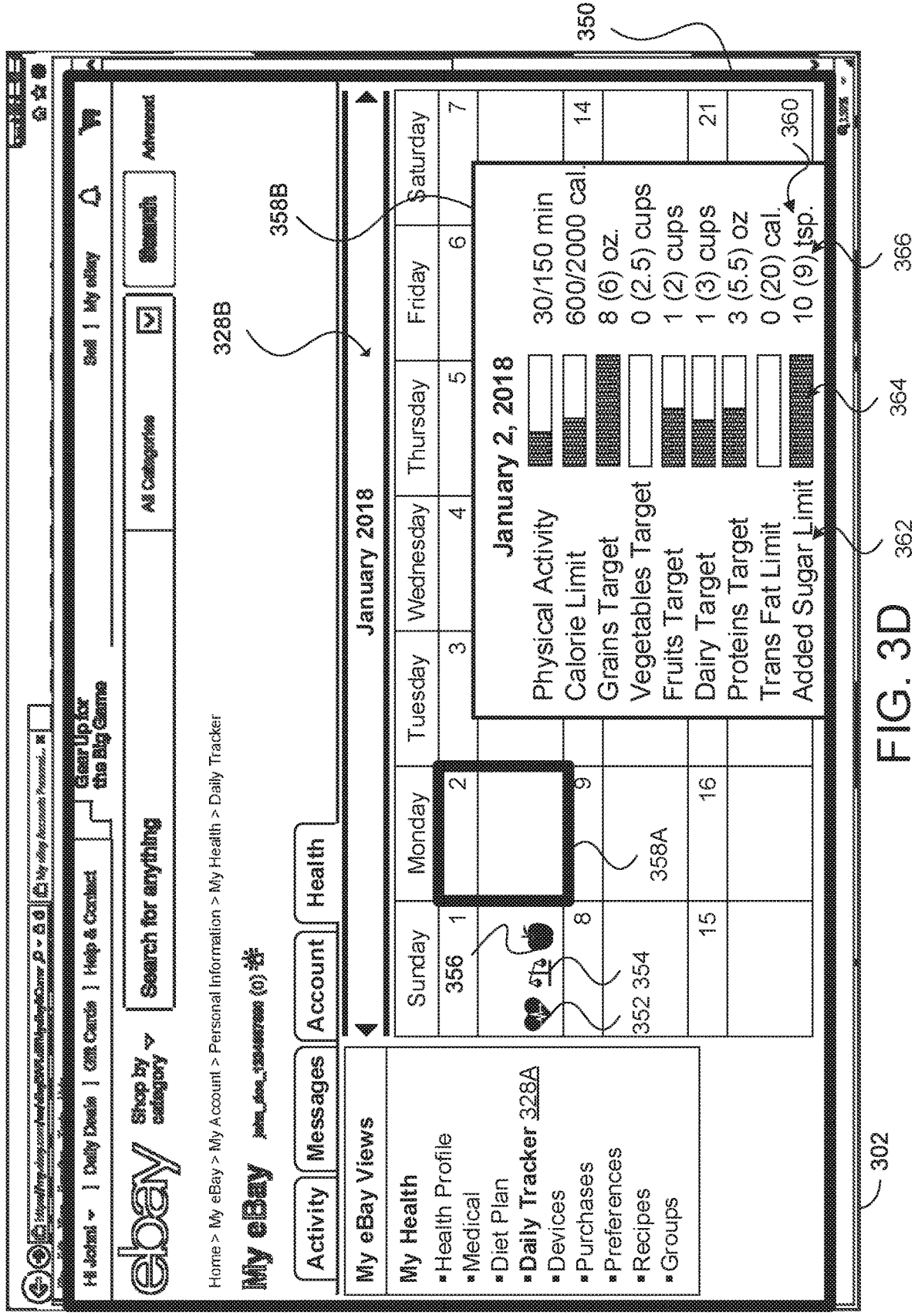

FIG. 3D shows an example of a graphical user interface, daily tracker 328B, which web browser 302 may present upon selection of daily tracker user interface selection element 328A. Daily tracker 328B may include a calendar interface that displays a high-level overview of a user's progress towards health, diet, and fitness goals. For example, daily tracker 328B may display user interface element 352 (e.g., a heart icon) to indicate that the user has achieved his fitness goal for the day, user interface element 354 (e.g., a scale icon) to indicate that the user successfully limited his daily calorie limit for the day, and user interface element 356 (e.g., an apple icon) to indicate that the user has achieved his food group targets for the day. Daily tracker 328B may display modified versions of user interface elements 352, 354, and 356 (e.g., completely grayed out, grayed out proportional to an extent the user failed to achieve a particular condition or goal, crossed out, etc.) or different user interface elements (e.g., sad face emoticons).

Daily tracker 328B can also include day user interface selection element 358A that enables the user to pick a particular day for a detailed view of user interface 358B of the user's progress towards his health, diet, and fitness goals or conditions. In this example, each row 360 of detailed view 358B can represent health, diet, or fitness goal or condition 362, graphical element 364 (e.g., a gauge) representing the extent the user has achieved the goal or condition, and user interface element 366 (e.g., text) indicating an actual amount of the condition or goal achieved by the user and the amount associated with the goal or condition in parenthesis.

Figure 3E:
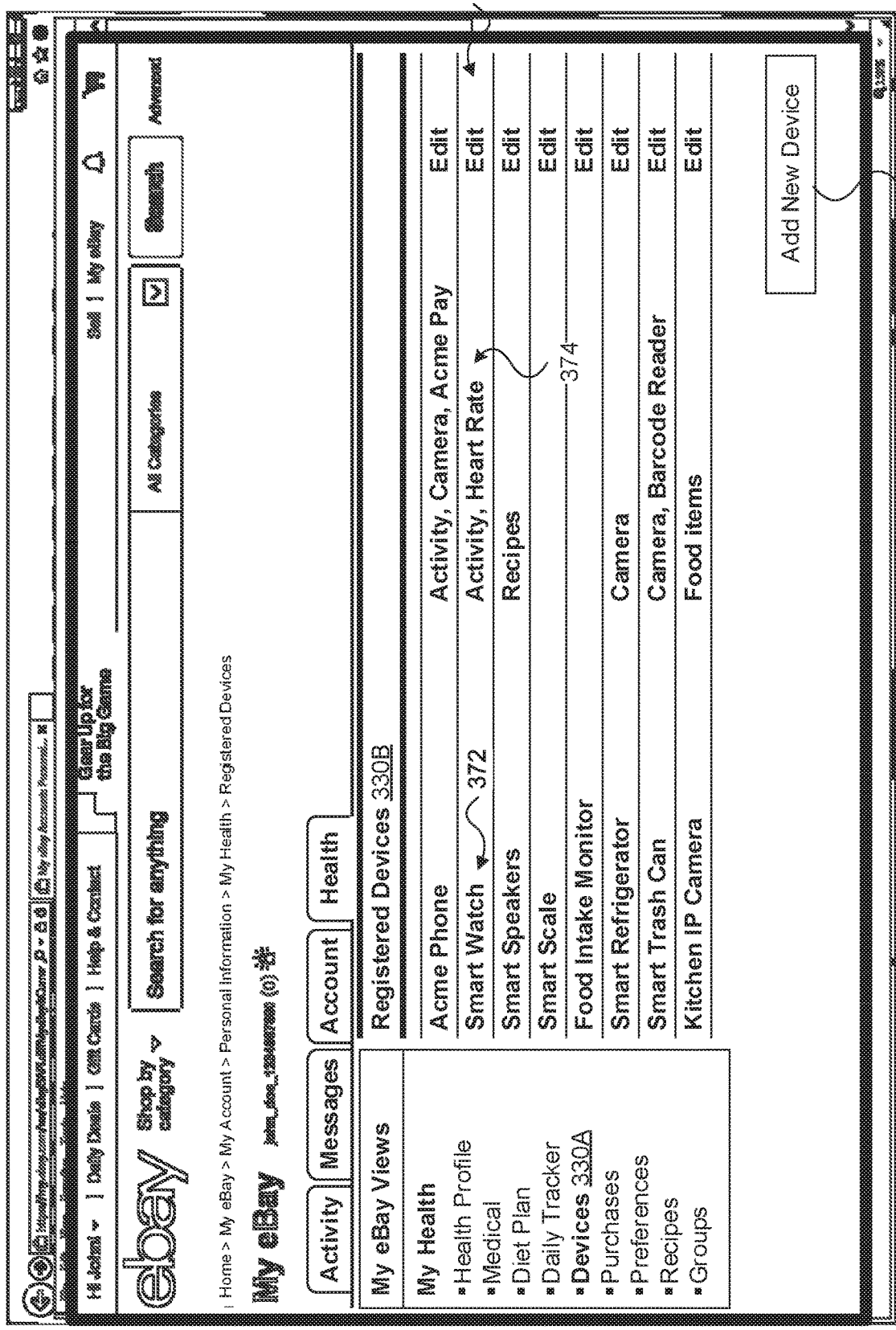

FIG. 3E shows an example of a graphical user interface, registered devices 330B, which may be presented by web browser 302 upon selection of registered devices user interface selection element 330A. In this example, each row of registered devices 330B represents a client device that the user has linked to his account with the network and limitations on the information to share information between the client device and the network. For example, in row 370, the user has authorized the network to receive information from client device 372 (e.g., a smart watch) but specifies limitation 374 that client device 372 may only share the user's activity information and heart rate information. The types of devices users may register with the network include any IoT device (e.g., IoT devices 203 of FIG. 2), mobile device (e.g., mobile devices 204 of FIG. 2), computing device (e.g., computing device 800 of FIG. 8), or any other electronic device capable of communicating (directly or indirectly) over a WAN.

Returning to FIG. 3B, selection of purchasing information user interface selection element 332 can navigate web browser 302 to a user interface for reviewing past purchases of food items from the network. In some embodiments, users may also be able to configure and review past purchases of food items from external sources (e.g., other online marketplaces, physical marketplaces, restaurants, etc.) that the user has authorized to share purchasing information.

Selection of dietary preferences user interface selection element 334 can navigate web browser 302 to a user interface for configuring a user's dietary preferences, such as favorite food items, disliked food items, favorite style of food (e.g., Italian, Ethiopian, Cuban, etc.), preferred brands (e.g., Land O Lakes® butter, Oroweat® bread, Oscar Meyer® deli meats, etc.), preferred farming style (e.g., organic, free-range, humane, etc.), preferred geographic origin (e.g., Napa wines, Georgia peaches, Maine lobster, etc.), and other favored characteristics of food items. In some embodiments, the network can automatically identify the user's dietary preferences from historical purchasing information, historical restaurant visits, medical information (e.g., physician's advice to follow a high-fiber diet, low-sodium diet from blood tests indicating high blood pressure, foods high in omega-3 fatty acids during pregnancy, etc.), and other user data streams indicative of the user's dietary habits.

Selection of recipe information user interface selection element 336 may navigate browser 302 to a user interface for saved recipes. The saved recipes can facilitate purchase of food items from the network, such as by including a user interface indicating availability of recipe ingredients at the online marketplace, a user interface element for automatically populating a virtual shopping cart with one or more of the recipe ingredients, recommendations for substitute ingredients to help the user achieve health and dietary goals, recommendations for preparing a recipe for an upcoming event (e.g., a spouse's favorite recipe on his/her birthday, a cookie recipe for a child's bake sale, a side dish recipe for a potluck, etc.).

Selection of groups user interface selection element 338 can navigate web browser 302 to a user interface for updating social information related to a user's health, diet, and fitness goals. For example, the groups user interface can allow the user to add family members, other household members, or other group members to help achieve those individuals' and/or group health and dietary goals. As another example, the groups user interface can enable the user to share health and dietary goals and progress towards the goals with other users. As yet another example, the groups user interface can provide visualizations to help the user track progress against other users having the same or similar demographic characteristics (e.g., age, gender, weight, height, etc.). In some embodiments, the network can also use information from the same or similar demography as a user prove recommendations regarding diet, exercise, and other user behavior.

Returning to FIG. 3A, selection of seller user interfaces selection 306 navigates web browser 302 to seller user interfaces of the network, such as user interfaces for creating listings, managing listings, and performing post-listing tasks. Selection of personalization user interface selection element 308 navigates web browser 302 to personalization user interfaces of the network, such as a dashboard summarizing a user's activities within the online marketplace, a user interface listing the user's most recently viewed item listings, a user interface listing the user's pending auction bids and sales offers, a user interface for monitoring item listings of interest to the user (e.g., a "watch" list), a user interface listing the user's selling activities in the online marketplace, a user interface of saved search queries, and other custom user interfaces.

Messaging user interface selection element 310 can operate to notify a user of new messages sent to the user, such as by changing its appearance (e.g., modifying its color, displaying additional graphical elements, etc.). In some embodiments, the network may display a number over messaging user interface selection element 310 to indicate the total of new messages sent to the user that the user has not read. Selection of messaging user interface selection element 310 can cause web browser 302 to present a summary view of the most recent messages received by the user. Alternatively or in addition, selection of messages user interface selection element 310 can navigate web browser 302 to an e-mail client or other electronic communication client that the user may utilize to draft and send new messages and manage received messages.

Keyword entry user interface element 312, category user interface selection element 314, and keyword search user interface element 316 enable a user to conduct keyword searches of the network. Users can enter search query terms into keyword entry user interface element 312, filter search results by category by selecting, category user interface selection element 314, and select keyword search user interface element 316 to execute the search.

Figure 3F:
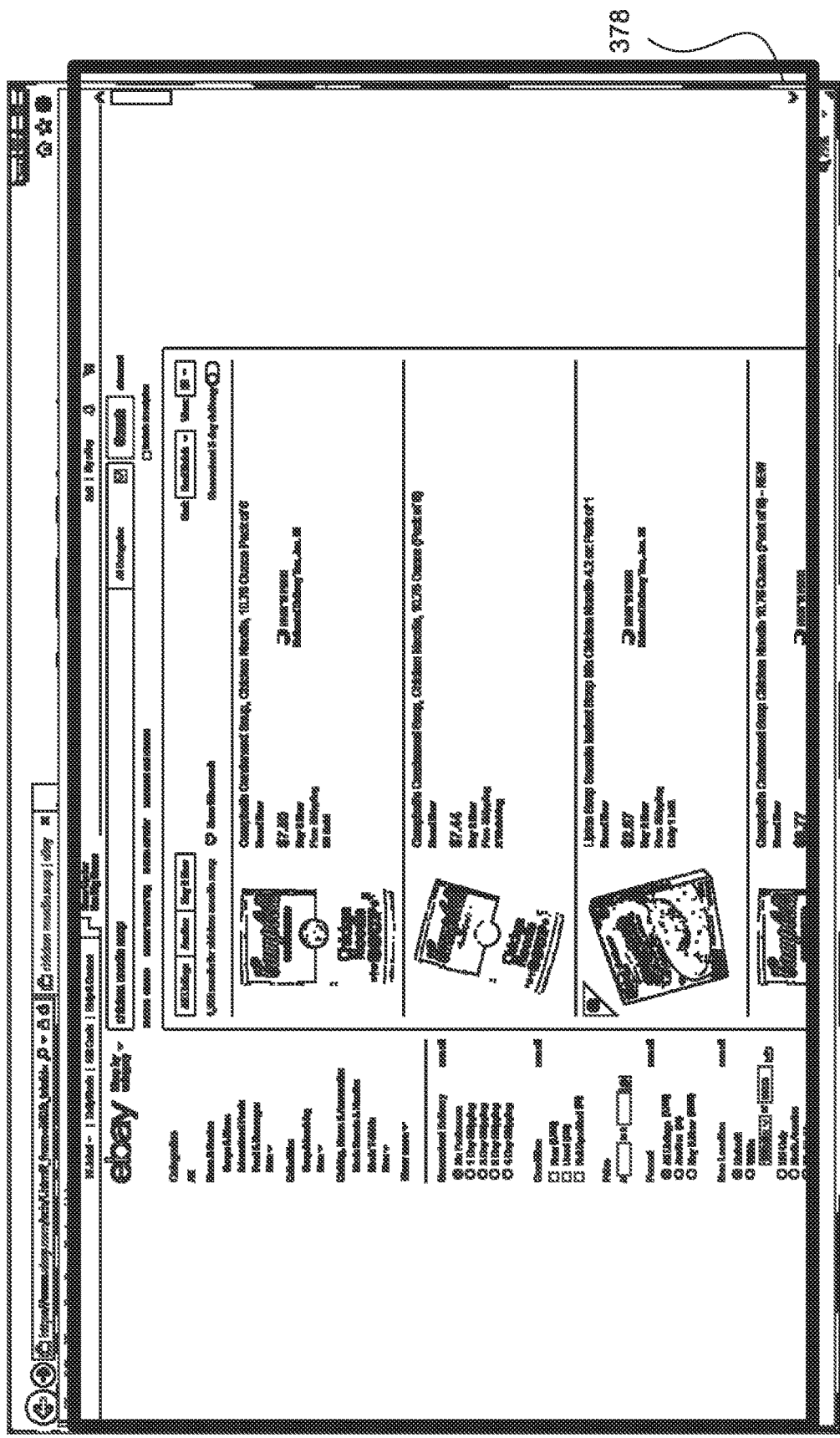
Figure 3G:
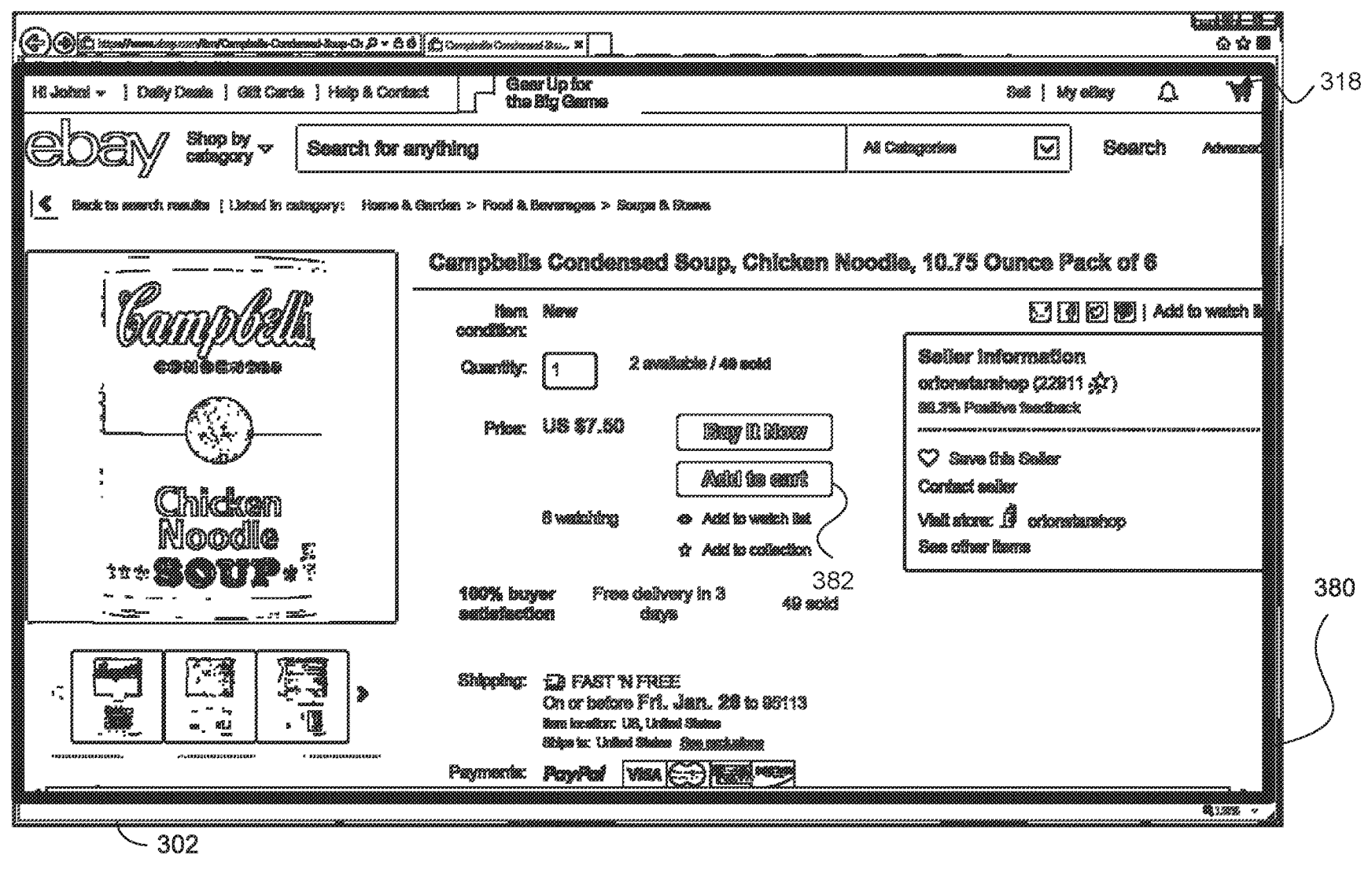

FIG. 3F shows an example of a graphical user interface, search results 378, of a set of item listings responsive to a search query, such as "chicken noodle soup." FIG. 3G shows an example of a graphical user interface, item listing 380, which web browser 302 can navigate to upon the user selecting one of the item listings from search results 378. Item listing 380 includes add to cart user interface selection element 382, that upon selection by the user, sends a request to the network to add the item associated with item listing 380 to a virtual shopping cart and trigger a smart virtual shopping cart service. The smart virtual shopping cart service may perform a series of operations to support the user's dietary goals. For example, the shopping cart service may perform a check to determine whether the item added to the virtual shopping cart is a food item. If so, the shopping cart service can next determine whether the user has set up a diet plan (e.g., diet plan 326B) with the network. If so, the shopping cart service can determine the user's progress towards his dietary goals during the current time period, such as by communicating with a quantitative analytical tool (e.g., quantitative consumption service 260) to determine the user's food consumption within the predetermined time period; the predicted nutritional values associated with purchasing the item, such as by communicating with a predictive analytical tool (e.g., predictive consumption service 262); and evaluate whether the predicted nutritional values may cause the user to fail to meet his dietary goals for the current time period in view of his consumption to date. If so, the virtual shopping cart service may issue appropriate warnings to the user.

FIG. 3H shows a few examples of alerts that the network may present to the user upon determining that one or more of the items he intends to purchase may cause him to fail to achieve a dietary goal. User interface 384 shows a warning to the user that purchasing the item is likely to cause him to exceed his weekly calorie limit. User interface 386 shows a warning that the item the user has selected for purchase may contain trace amounts of one of the user's known allergens. User interface 388 shows a warning that the user may not meet his daily target of cups of vegetables each day. On the other hand, if the virtual shopping cart service determines that the user's purchase is not likely to cause him to fail to meet one of his dietary goals, the network may allow the user to continue with the purchase. FIG. 3I shows an example of a graphical user interface, checkout 390, permitting the user to proceed to payment for the item.

Figure 4:
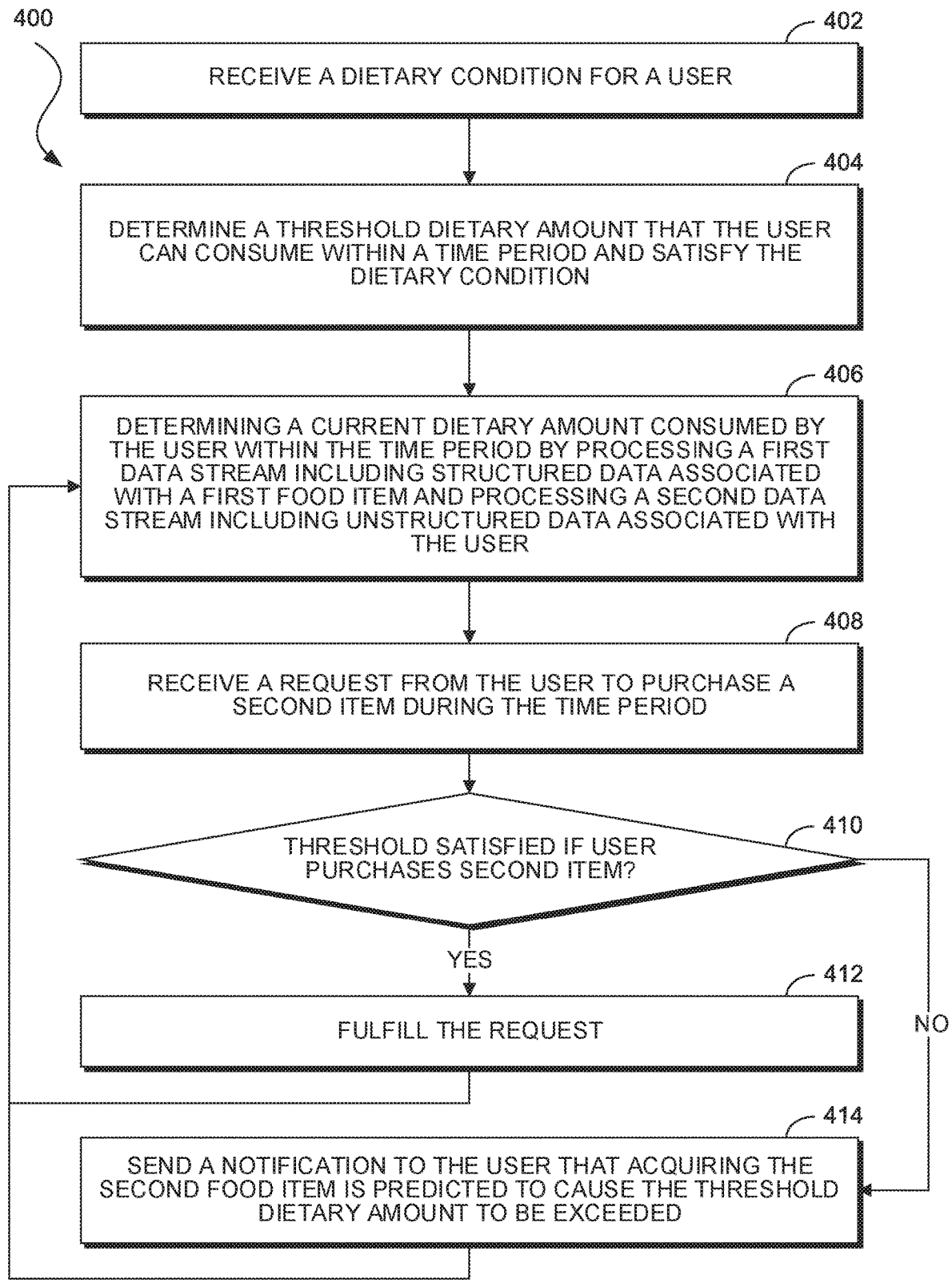
FIG. 4 illustrates an example of a process for providing smart virtual shopping cart functionality in accordance with an embodiment.

FIG. 4 shows an example of a method, process 400, for providing smart virtual shopping cart functionality to facilitate user adherence to dietary plans. For any method or process discussed in the present disclosure, there can be additional, fewer, or alternative steps performed that occur in similar or alternative orders, or in parallel, within the scope of various embodiments unless otherwise stated. For illustrative purposes, a network including online marketplace functionality (e.g., network 210 of FIG. 2 or network 502 of FIG. 5) can perform process 400 but one of ordinary skill in the art will appreciate that other embodiments may utilize other types of network services and applications to perform process 400.

Process 400 can begin at step 402 in which the network can receive dietary goals or conditions for a user or a group of users. In some embodiments, the user or group of users can input the dietary conditions via a user interface (e.g., user interface 326B of FIG. 3C) provided by the network or select from a set of diet plans (e.g., DASH, TLC, and Mayo Clinic® diets) or dietary goals (e.g., weight loss, reduce sodium intake, increase good cholesterol intake/reduce bad cholesterol intake, etc.). In the event users select from the set of diet plans or dietary goals, the network can automatically determine the users' dietary conditions based on their selection. In other embodiments, the network may automatically select the dietary goals or conditions based on a medical professional's advice to the user, governmental dietary guidelines, historical information of similar users, or a combination of these techniques (e.g., average, median, weighted combination, machine learning evaluation, etc.).

At step 404, the network can determine threshold dietary amounts that the user or group of users can receive over a predetermined time period that will satisfy the dietary goals or conditions. In some embodiments, the thresholds can represent a ceiling or cap for prescribing consumption (e.g., calories, salt, sugar, or other food items/ingredients affecting dietary conditions the user should lower intake of or limit) or conduct (e.g., smoking, sunbathing/staying out in the sun, etc.). In other embodiments, the thresholds can represent a floor or a bottom of consumption (e.g., food items/ingredients containing higher sources of HDL, Omega-3 fatty acids, items of a particular food group, etc.) or activity (e.g., exercise, sleep, etc.). Thus, dietary targets can define minimum thresholds that must be exceeded to satisfy a particular dietary goal or condition (e.g., amounts of nutrients, vitamins, minerals, etc.), or maximum thresholds not to be exceeded to satisfy a corresponding dietary goal or condition (e.g., calories, added sugar, sodium, etc.). The predetermined time period can be specified by the user or group of users, a medical professional, a governmental guideline, or the network evaluating one or more of these data sources. Dietary targets may occur daily, weekly, bi-weekly, monthly, annually, or by other suitable time interval.

Process 400 can proceed to step 406 in which the network can monitor dietary amounts consumed by the user within the predetermined time period. This can involve processing multiple heterogeneous data streams, including data streams from the user's or group of users' IoT devices, mobile devices, shopping history data repositories of the network and networks external to the network (e.g., online marketplaces, online restaurant or food delivery services, online grocery or ingredient-and-recipe meal kit services, and other e-commerce services and applications), social networks, and third-party user application data repositories, among other sources. These data streams include heterogenous data in several senses, including heterogeneity in structure (e.g., structured, semi-structured, and unstructured); in data type (e.g., text, image, audio, video, etc.); in type of data store (e.g., relational databases, key-value stores, document databases, graph databases, column-family databases, data analytic stores, search engine databases, time series databases, object store, file systems, etc.), in source (e.g., CRM, ERP, SCM, clickstream, social networks, devices and sensors, logs, etc.), in processing rate (e.g., streaming, batch, etc.), or other basis of differentiation discussed throughout the present disclosure.

In some embodiments, the network can utilize a distributive processing framework (e.g., MPP, MapReduce, Spark™, etc.) for collecting, transforming, and storing the heterogeneous data streams; integrating the data to provide access to all data sources and to support different modes of access (e.g., EDW, data lake, data virtualization, etc.); and exposing optimized views (e.g., data marts, operational data stores, analytic sandboxes, etc.) of the integrated data to support the services of the network. For example, a user may be associated with an unstructured data stream comprising images of food items consumed by the user within a predetermined time period (e.g., the user may take photos of one or more of his/her meals and explicitly share it with the network for the network to identify the food items, determine their nutritional values, and analyze how the nutritional values affect the user's dietary goals and conditions; the user shares photos of a meal over social media and the network scrapes the photos to perform similar analysis on the user's behalf; the network conducts forensic analysis from image data captured by the user's registered IoT devices, mobile devices, and wearable devices and publicly available image data captured by other devices and sensors; etc.). Alternatively or in addition, the network can piece together the user's meals over the predetermined time period from online purchases; mobile device or credit card payments to brick-and-mortar stores, restaurants, and the like; requests to a digital assistant device (e.g., smart home speaker) for recipes; historical user behavior data; and other data streams.

At step 408, the network can receive a request from a user or group of users to add or more food items listed by the network to a virtual shopping cart. In various embodiments, the network includes virtual shopping cart functionality that enables a user to add items to a virtual shopping cart and continue browsing the network or perform other tasks within the network before proceeding to checkout and paying for items saved to the cart. In some embodiments, the network can pre-cache or pre-load into memory data relating to the user's dietary goals and conditions, food items consumed by the user during the predetermined time period, nutritional values associated with the consumed food items and items saved to the virtual shopping cart, and other data that the network will later need to fetch at conditional step 410 to determine whether purchasing items in the virtual shopping cart will satisfy the dietary thresholds determined during step 404. In this example, the network can operate as a general online marketplace that sells a wide variety of goods and services. However, when the user populates the virtual shopping cart with at least one food item, the network must evaluate the user's dietary goals and conditions, the food items the user has consumed during the predetermined time period, nutritional values associated with the consumed food items and food items in the virtual shopping cart. The network can decrease latency for these tasks by pre-caching or pre-loading this data into memory. Such an approach can be especially advantageous when the network uses an in-memory processing framework, such as the Spark™ processing framework.

In some embodiments, the user may forego adding food items to a shopping cart and instead immediately proceed to checkout upon selecting one or more food items. The network can nevertheless invoke the virtual shopping cart service to ensure that purchase of the food items does not cause the user or group of users to meet their dietary goals and conditions. In some embodiments, the network may not wait until checkout to invoke the virtual shopping cart service and may immediately apply the virtual shopping cart service functionality and issue warnings, recommend substitute food items, or take other appropriate actions as soon as the network predicts that purchasing an item will cause the user or group of users to fail to achieve their dietary goals and conditions.

At conditional step 410, the network can determine whether the user's purchase of the items in the virtual shopping cart will cause the user to fail to meet his/her dietary goals and conditions. This can be achieved using quantitative consumption and predictive consumption services, such as discussed with respect to quantitative consumption and predictive consumption services 260 and 262 of FIG. 2, respectively. Quantitative consumption services can determine a current a dietary amount of consumption over a specified time period, and may include identifying food items and ingredients purchased over a predetermined period of time from the online marketplace or other network services and applications capturing user data and made available to the network (e.g., a food purchasing data stream generally comprising structured data). Quantitative consumption services can also include quantify nutritional data of food items consumed by the user from image/video data (e.g., an image/video data stream generally comprising unstructured data). These services can also include tracking food intake monitoring data that measure the number of bites, chews, or swallows that the user makes and correlates those numbers to amounts of consumption (alone or combined or "fused" with analysis of image/video data, purchasing data, etc.) or ingestible sensors capable of measuring digested amounts of food. Quantitative consumption services may include monitoring user consumption habits, such as the user drinking a can of beer every evening, ordering a particular food item once a week, or eating a granola bar after every run, among regular user behavior. Although the quantitative consumption services may not always be accurate, it can still be helpful for this information to be automatically generated and corrected by the user than to manually determine this information outright. In addition, corrections can be provided as additional data points for improving the quantitative consumption services.

Predictive consumption services can determine an updated dietary amount to be consumed within a specified time period by aggregating the current dietary amount identified by quantitative consumption services and a predicted dietary amount, such as a likely amount of food consumed when purchasing a particular item. Thus, the predictive consumption services may use the same or similar data sources as the quantitative consumption services, including user behavior data, sensor data, purchasing history data, dietary application data, or data fusion of multiple data streams. For example, the network can monitor the user's and/or the user's cohorts' eating habits over a statistically significant period of time to determine that the user consumes 80% of the food he purchases from an online marketplace every week. When the user purchases groceries for a given week, the network can predict the number of calories consumed that week by that week's grocery purchases. Alternatively or in addition, the network can determine a number of meals the user will eat at home based on the week's purchases and rely on past data indicating that the user will eat out the remaining days of the week and that the user consumes 1,500 calories when he eats at a restaurant. Alternatively or in addition, the network can analyze a subset of consumption data determined by quantitative consumption services as training data for machine learning classification, extract features (e.g., number of calories from grocery store purchases, number of calories from eating out, number of calories eaten for a particular day of the week, number of calories consumed when eating during a particular time of day, number of calories of a meal including a particular item, etc.), determine a parameterized machine learning model from the extracted features, and apply known parameters to the model to predict the user's expected amount of consumption over a specified time period.

In some embodiments, the network can optimize the performance of step 410 by exposing a view (e.g., data mart, operational data store, etc.) into the data storage layer (e.g., data storage layer 140 or HDFS™ 240, data warehouse 242, and data virtualization layer 244 of FIG. 2) of the network that is most efficacious to this use case. This can depend on the type of data store (e.g., relational database, key-value store, column family, etc.) used to persist information from each relevant data stream and data source, the data type of the data, the structure of the data, and other factors.

If purchasing the items within the predetermined time period satisfies the dietary thresholds determined during step 404, process 400 can proceed to step 412 and the network can fulfill the user's request and process the items in the user or group of users' virtual shopping cart for payment and delivery. The network can then return to step 406 and continue monitoring food intake until the predetermined time period ends and begin user monitoring consumption for the next time period. In some embodiments, the network can also provide notifications to users near the end of the predetermined time period if they have not yet achieved certain dietary targets. The notifications can identify potentially missed targets and provide recommendations for food items the user can purchase to meet those targets.

If at conditional step 410, the network predicts that purchasing the items within the predetermined time period would cause the user or group of users to fail to meet their dietary goals and conditions, the network can provide an alert to warn them of the potential failure at step 414. In one embodiment, the alert can be represented graphically by showing image data of the virtual shopping cart overflowing to prompt users to re-assess their purchases. In other embodiments, the network may display gauges representing users' current consumption rates proportional to the threshold dietary amounts, as shown in user interface 358B of FIG. 3D. In still other embodiments, the network can present a warning during checkout, such as user interfaces 384, 386, and 388 of FIG. 3H. Alternatively or in addition, the network can send the user or group of users a warning via e-mail, text message, mobile app notification, or other electronic communication. In addition, the network can present recommendations for substitute items that will satisfy the dietary thresholds to accompany the various alerts and warnings.

Figure 5:
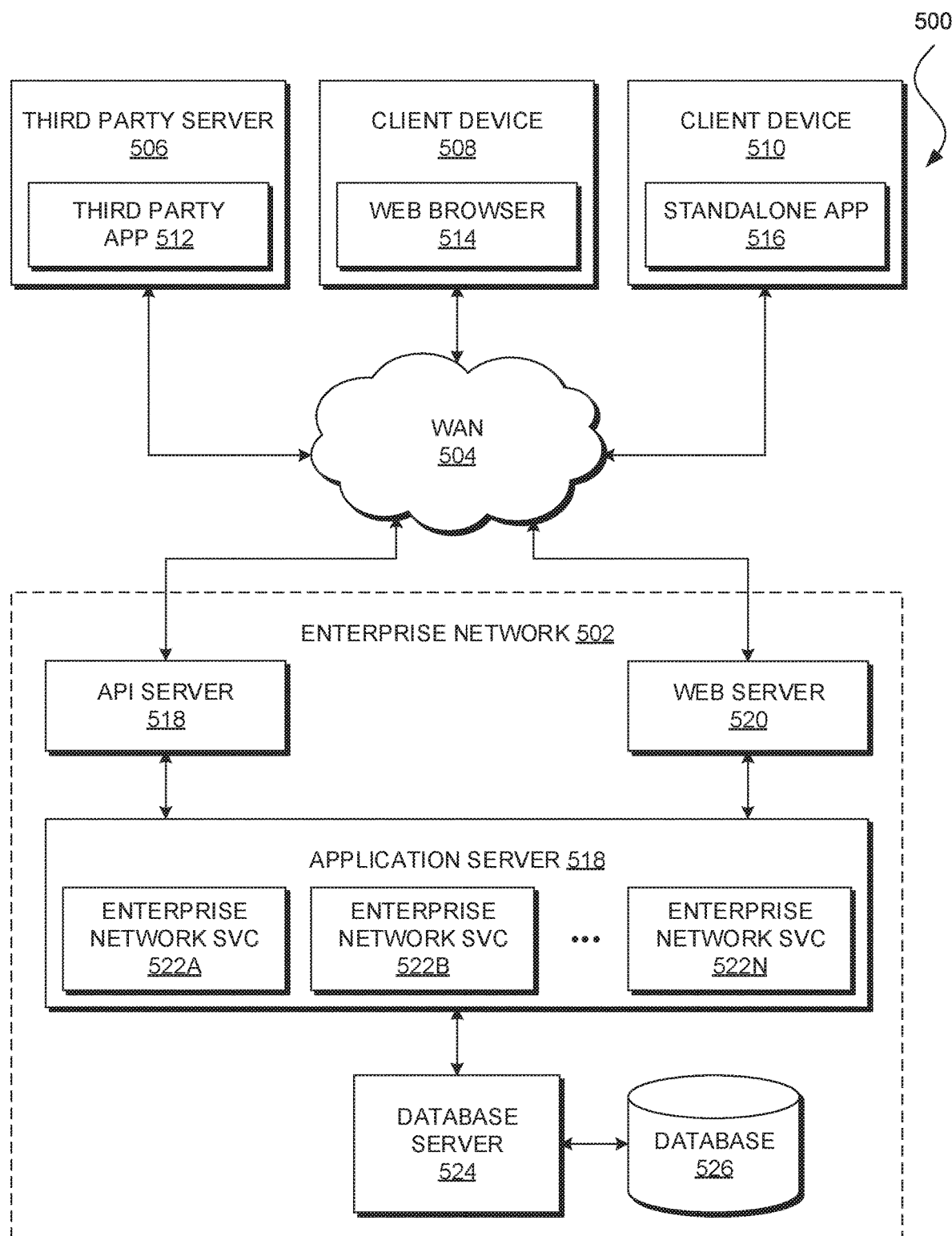
FIG. 5 illustrates an example of a network environment in accordance with an embodiment.

FIG. 5 shows an example of an application architecture, application architecture 500, in which various embodiments of the present disclosure may be deployed. In this example, application architecture 500 includes network 502, wide area network (WAN) 504 (e.g., the Internet), third party server 506, client device 508, and client device 510. Network 502 can provide online marketplace functionality to third party server 506, client device 508, and client device 510 over WAN 504. Users (e.g., buyers, sellers, advertisers, etc.) may interact with network 502 using third party application 512 (e.g., applications incorporating the eBay® API), web browser 514 (e.g., Microsoft Internet Explorer®, Google Chrome®, Mozilla Firefox®, Apple Safari®, etc.), or standalone application 516 (e.g., eBay® mobile app for Google Android®, Apple iOS®, etc.) executing on third party server 506, client device 508, and client device 510, respectively. Although each of third party server 506, client device 508, and client device 510 are shown executing one application to interact with network 502, each may include third party application 512, web browser 514, standalone application 516, or some combination of these applications.

Some examples of client devices 508 and 510 include servers, desktop computers, mobile phones, smart phones, tablets, ultra-books, netbooks, laptops, multi-processor systems, microprocessor-based or programmable consumer electronics, game consoles, set-top boxes, or any other communication device that a user may utilize to access network 502. An example of an implementation of client device 508 and/or 510 is discussed further below with respect to FIG. 8.

Application program interface (API) server 518 and web server 520 may be coupled to, and provide programmatic and web interfaces respectively to, application server 518. Application server 518 may host network services 522A, 522B, . . . 522N (collectively, 522), each of which may comprise one or more modules or applications embodied as hardware, software, firmware, or any combination thereof. Application server 518 may connect to database server 524 to access information storage repository or database 526. In some embodiments, database 526 is a storage device that stores information to be posted (e.g., publications or listings, images of products, etc.) to network services 522. Database 526 may also store digital goods information in accordance with various embodiments.

Web browser 514 can access various network services 522 via a web interface supported by web server 520. Similarly, standalone client application 516 can access the various services and functions provided by network 502 via the programmatic interface provided by API serve 518, in some embodiments, standalone client application 508 may be a seller application (e.g., the Turbo Lister application developed by eBay® Inc.) to enable sellers to author and manage listings on network 502 in an off-line manner, and to perform batch-mode communications between standalone client application 516 and network 502.

Additionally, third-party application 512, executing on a third-party server 506, may have programmatic access to network 502 via the programmatic interface provided by API server 518. For example, third-party application 512, utilizing information retrieved from network 502, may support one or more features or functions on a website hosted by the third-party. The third-party website may provide one or more promotional, marketplace, or payment functions that are supported by the relevant applications of the network 502.

Figure 6:
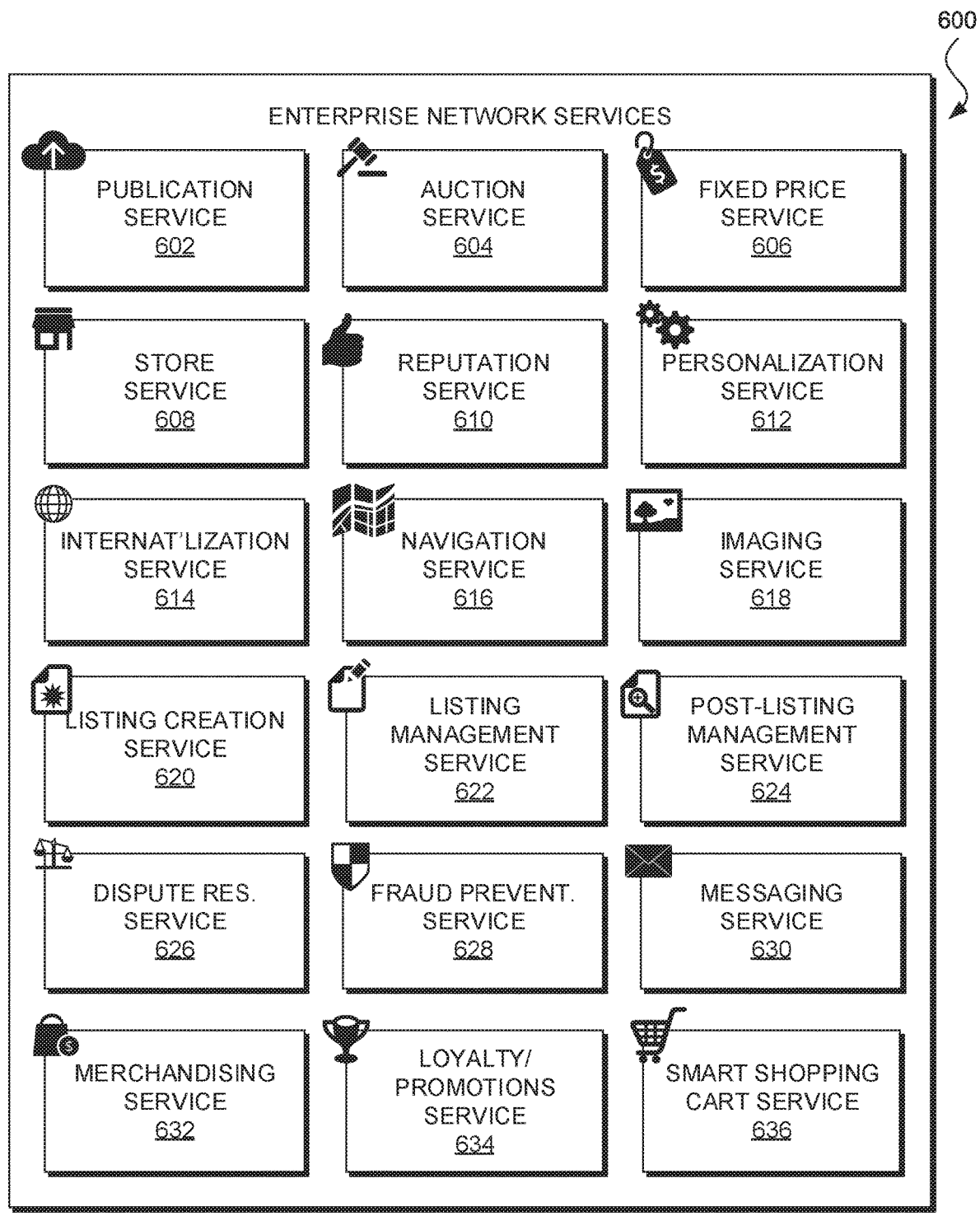
FIG. 6 illustrates an example of a services architecture for providing smart virtual shopping cart functionality in accordance with an embodiment.

FIG. 6 shows an example of a service architecture comprising network services 600 that a network (e.g., network 210 of FIG. 2 or network 502 of FIG. 5) can operate for providing smart virtual shopping cart functionality. For illustrative purposes, network services 600, in this example, provide certain functionality to users of an online marketplace, such as enabling sellers to add or edit item listings and associated content (e.g., text descriptions of the item listings, photos associated with the item listings, videos associated with the item listings, etc.), allowing buyers to review the item listings (e.g., examine detailed descriptions of item listings, search item listings by keyword or image query, receive recommended item listings, etc.), facilitating the sales or exchange of the item listings (e.g., auctions, fixed price sales, returns, etc.), and the like. Network services 600 may be physically located on-premises (e.g., hosted within one or more data centers owned or leased by an enterprise), off-premises (e.g., hosted by a public cloud provider, data center provider, etc.), or both (e.g., hosted using a hybrid cloud environment). Thus, network services 600 can run in dedicated or shared servers that are communicatively coupled to enable communications between the servers. Network services 600 themselves can be communicatively coupled (e.g., via appropriate interfaces) to each other and to various data sources to allow information to be passed between the services or allow the services to share and access common data.

In this example, network services 600 include publication service 602, auction service 604, fixed-price service 606, store service 608, navigation service 610, personalization service 612, internationalization service 614, navigation service 616, imaging 618, listing creation service 620, listing management service 622, post-listing management service 624, dispute resolution service 626, fraud prevention service 628, messaging service 630, merchandising service 632, loyalty/promotions service 634, and smart virtual shopping cart service 636. One of ordinary skill in the art will appreciate that other embodiments may utilize different sets of services, including configurations with more services, fewer services, or alternative services, for providing online marketplace functionality.

Publication service 602 can publish information, such as item listings or production description pages. Auction service 604 can support auction-format listing and other variable price-setting mechanisms (e.g., English, Dutch, Vickrey, Chinese, Double, Reverse auctions etc.). In some embodiments, auction service 604 may also provide a number of features in support of auction-format listings, such as a reserve price feature in which a seller may specify a minimum price that must be exceeded in order for a winning bidder to receive an item in connection with a listing or a proxy-bidding feature in which a buyer may specify a maximum price not to be exceeded by an agent bidding on the buyer's behalf.

Fixed-price service 606 can support fixed-price listing formats (e.g., traditional classified advertisement-type listing or a catalogue listing) and buyout-type listings (e.g., the Buy-It-Now (BIN) technology developed by eBay® Inc.). In some embodiments, buyout-type listings may be offered in conjunction with auction-format listings, and allow a buyer to purchase items (e.g., goods or services), that may also be offered for sale via an auction, for a fixed-price that is typically higher than the starting price of the auction.

Store service 608 can allow a seller to group listings within a "virtual" store, which can include items branded and otherwise personalized by and for the seller. In some embodiments, store service 608 may also provide functionality for sellers to offer promotions, incentives, and features that are specific and customized for the seller.

Reputation service 610 can allow users to establish, build, and maintain reputations in an online marketplace. In some embodiments, reputation service 610 can publish users' reputations to potential trading partners. For example, an online marketplace may support person-to-person trading but users may have no history or other reference information to determine the trustworthiness and credibility of potential trading partners. Reputation service 610 can allow a user to establish a reputation within the online marketplace over time, such as through feedback provided by other transaction partners. Other potential trading partners may then reference such a reputation for the purposes of assessing credibility and trustworthiness.

Personalization service 612 can allow users to customize various aspects of their interactions with an online marketplace. For example, a user may create a personalized reference page on which information regarding transactions to which the user is (or has been) a party may be viewed. Further, personalization service 612 may enable users to customize listings and other aspects of their interactions with the online marketplace and other parties. In some embodiments, personalization service 612 may enable a user to input, select, authorize access to, or otherwise manage various data streams associated with the user's health, diet, and fitness, such as shown in user data sources 202 of FIG. 2 and the graphical user interfaces of FIGS. 3B-3E.

In some embodiments, an online marketplace may be organized according to language (e.g., English, Spanish, Mandarin, etc.), geographic region (e.g., Europe, United Kingdom, Scotland, etc.), demographic group (e.g., French Canadians, Basques, Cantonese-speaking Chinese, etc.), or other categorization. For ample, one version of the online marketplace may be customized for the United Kingdom, while another version of the online marketplace may be customized for the United States. Each of these versions may operate as an independent marketplace or may be customized (or internationalized) presentations of a common underlying marketplace. Accordingly, the online marketplace may include internationalization service 614 for providing customized information (and/or the presentation of information) by the online marketplace according to predetermined criteria (e.g., lingual, geographic, demographic, or similar criteria).

Navigation of an online marketplace may be facilitated by navigation service 616. In some embodiments, navigation service 616 can include a search service to enable keyword searches of listings published in the online marketplace. In some embodiments, navigation service 616 can also support image searches by receiving an image of an item (e.g., a query image) and providing item listings of items similar to the query. In some embodiments, navigation service 616 can include a browse service that allows users to browse various category, catalogue, or inventory data structures according to which listings may be classified within the online marketplace. Various other navigation services may also be provided to supplement the search and browsing services.

In order to make listings of an online marketplace as visually informative and attractive as possible, network services 600 may include imaging service 618 to enable users to upload images with listings. In some embodiments, imaging service 618 can also search for images related to a listing and incorporate the related images within the listings. In some embodiments, imaging service 618 may also support one or more promotional features, such as image galleries that are presented to potential buyers. For example, sellers may pay an additional fee to have an image included within a gallery of images for promoted items.

Listing creation service 620 can allow sellers to conveniently author listings pertaining to items (e.g., goods or services) that they wish to transact via an online marketplace. Listing management service 622 can allow sellers to manage such listings. For example, a seller may author and/or publish a large number of listings within the online marketplace. The management of such listings may present the user a challenge. Listing management service 622 can provide a number of features (e.g., auto-relisting, inventory level monitors, etc.) to assist the seller in managing such listings. Post-listing management service 624 can also assist sellers with a number of activities that typically occur after expiration of listings. For example, upon completion of an auction facilitated by auction service 604, a seller may wish to leave feedback regarding a particular buyer. Post-listing management service 624 may provide an interface to reputation service 610 to allow the seller to provide feedback regarding multiple buyers.

Dispute resolution service 626 can provide mechanisms in which disputes arising between transacting parties may be resolved. For example, dispute resolution service 626 may provide guided procedures to direct the parties through a number of steps in an attempt to settle a dispute. In the event that the dispute cannot be settled via the guided procedures, the dispute may be escalated to a third-party mediator or arbitrator.

Fraud prevention service 628 can implement fraud detection and prevention mechanisms to reduce the occurrence of fraud within an online marketplace.

Messaging service 630 can be responsible for the generation and delivery of messages to users of an online marketplace. For example, messaging service 630 can transmit messages regarding the status of listings within the online marketplace (e.g., "outbid" notices to bidders, notifications indicating that a bidder has won an auction, reminders to sellers to ship items, reminders to buyers to pay for items, etc.). Messaging service 630 may utilize any message delivery networks and platforms to deliver messages to users. For example, messaging service 630 may deliver electronic mail (e-mail), instant messages (IMs), Short Message Service (SMS) text messages, facsimiles, or voice messages (e.g., Voice over IP (VoIP)) over various telecommunication networks, such as the Internet, Plain Old Telephone Service (POTS) networks, cellular networks, WIFI networks, etc.).

Merchandising service 632 can support various merchandising functions that are made available to sellers to increase sales in an online marketplace. Merchandising service 632 can also operate the various merchandising features that may be invoked by sellers, and may monitor and track the success of merchandising strategies employed by sellers.

An online marketplace, or one or more parties entering into transactions in the online marketplace, may operate loyalty programs supported by loyalty/promotions service 634. For example, a buyer may earn loyalty or promotion points for each transaction established and/or concluded with a particular seller, and be offered a reward for which accumulated loyalty points can be redeemed.

Smart virtual shopping cart service 636 can operate in conjunction with other services to support users' health, diet, and fitness goals. For example, smart virtual shopping cart service 636 can communicate with personalization service 612 to receive a user's personal information and devise a diet plan for that user. In addition, smart virtual shopping cart service 636 may interact with fixed-price service 606 and store service 608 to evaluate the user's purchases of food items over a specified period of time and to determine the extent to which the user is likely to achieve those goals. In some embodiments, smart virtual shopping cart service 636 may also interact with imaging service 618 to identify items consumed by the user over the specified period of time. For example, if the user has purchased bagels and cream cheese within the last week from fixed-price service 606, then imaging service 618 can more easily match image/video data of food items eaten by the user within the past few days at breakfast to stored image data of the bagels or brand of the cream cheese purchased by the user.

Figure 7:
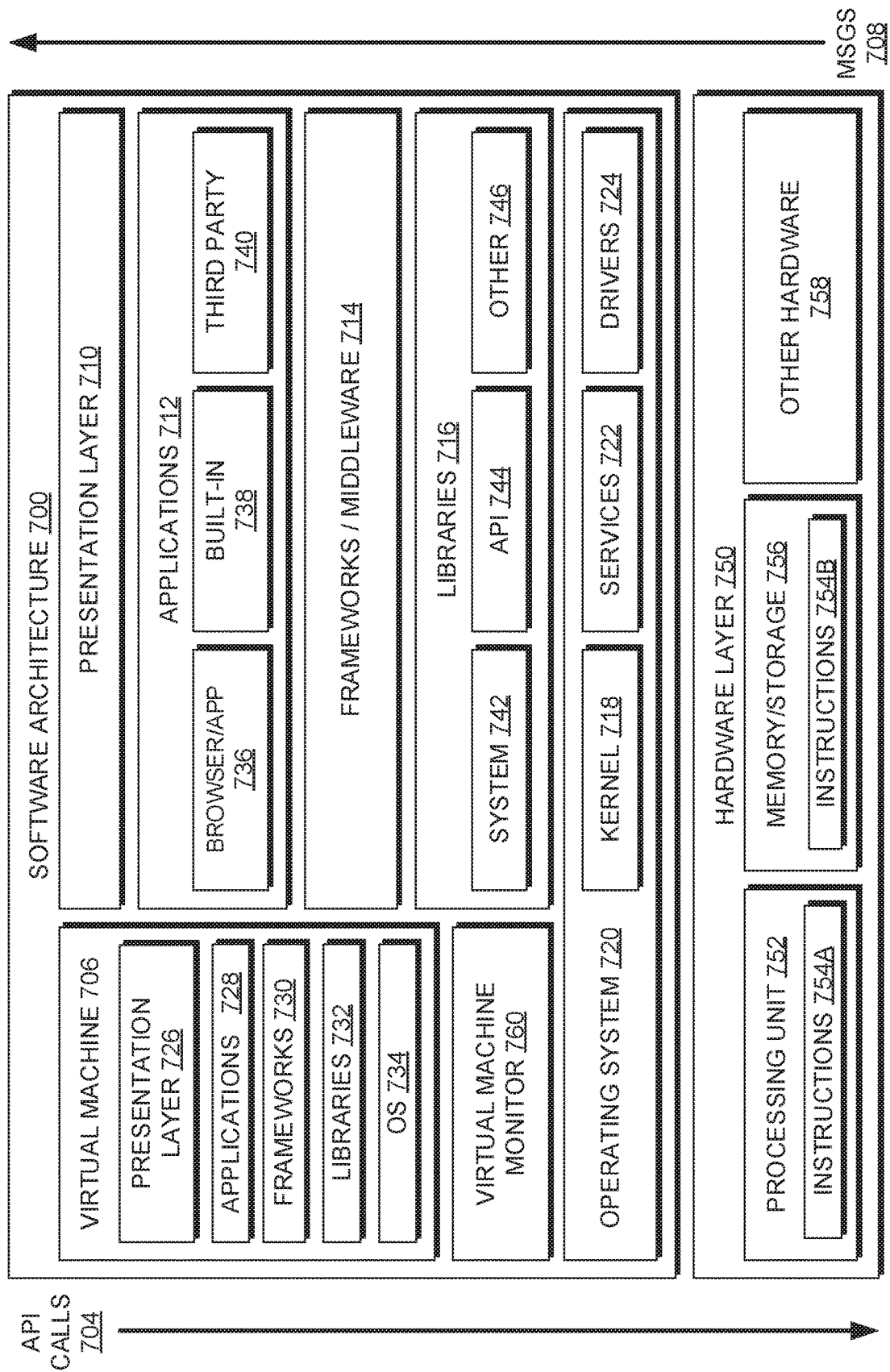
FIG. 7 illustrates an example of a software architecture in accordance with an embodiment.

FIG. 7 shows an example of a software architecture, software architecture 700, that various hardware devices described in the present disclosure can implement. Software architecture 700 is merely one example of a software architecture for implementing various embodiments of the present disclosure and other embodiments may utilize other software architectures to provide the functionality described herein. Software architecture 700 may execute on hardware, such as computing system 800 of FIG. 8. Hardware layer 750 can represent a computing system, such as computing system 800 of FIG. 8. Hardware layer 750 can include one or more processing units 752 having associated executable instructions 754A. Executable instructions 754A can represent the executable instructions of software architecture 700, including implementation of the methods, modules, and so forth of FIGS. 1, 2, 3A-3I, 4, 5, and 6. Hardware layer 750 can also include memory and/or storage modules 756, which also have executable instructions 754B. Hardware layer 750 may also include other hardware 758, which can represent any other hardware, such as the other hardware illustrated as part of computing system 800.

In the example of FIG. 7, software architecture 700 may be conceptualized as a stack of layers in which each layer provides particular functionality. For example, software architecture 700 may include layers such as operating system 720, libraries 716, frameworks/middleware 714, applications 712, and presentation layer 710. Operationally, applications 712 and/or other components within the layers may invoke API calls 704 through the software stack and receive a response, returned values, and so forth as messages 708. The layers illustrated are representative in nature and not all software architectures have all layers. For example, some mobile or special-purpose operating systems may not provide a frameworks/middleware layer 714, while others may provide such a layer. Other software architectures may include additional or different layers.

Operating system 720 may manage hardware resources and provide common services. In this example, operating system 720 includes kernel 718, services 722, and drivers 724. Kernel 718 may operate as an abstraction layer between the hardware and the other software layers. For example, kernel 718 may be responsible for memory management, processor management (e.g., scheduling), component management, networking, security settings, and so on. Services 722 may provide other common services for the other software layers. Drivers 724 may be responsible for controlling or interfacing with the underlying hardware. For instance, drivers 724 may include display drivers, camera drivers, Bluetooth drivers, flash memory drivers, serial communication drivers (e.g., Universal Serial Bus (USB) drivers), Wi-Fi drivers, audio drivers, power management drivers, and so forth depending on the hardware configuration.

Libraries 716 may provide a common infrastructure that may be utilized by applications 712 and/or other components and/or layers. Libraries 716 typically provide functionality that allows other software modules perform tasks in an easier fashion than to interface directly with the underlying operating system functionality (e.g., kernel 718, services 722, and/or drivers 724). Libraries 716 may include system libraries 742 (e.g., C standard library) that may provide functions such as memory allocation functions, string manipulation functions, mathematic functions, and the like. In addition, libraries 716 may include API libraries 744 such as media libraries (e.g., libraries to support presentation and manipulation of various media format such as MPEG4, H.264, MP3, AAC, AMR, JPG, PNG), graphics libraries (e.g., an OpenGL framework that may be used to render 2D and 3D graphics for display), database libraries (e.g., SQLite that may provide various relational database functions), web libraries (e.g., WebKit that may provide web browsing functionality), and the like. Libraries 716 may also include a wide variety of other libraries 746 to provide many other APIs to applications 712 and other software components/Modules.

Frameworks 714 (sometimes also referred to as middleware) may provide a higher-level common infrastructure that may be utilized by applications 712 and/or other software components/modules. For example, frameworks 714 may provide various graphic user interface (GUI) functions, high-level resource management, high-level location services, and so forth. Frameworks 714 may provide a broad spectrum of other APIs that may be utilized by applications 712 and/or other software components/modules, some of which may be specific to a particular operating system or platform.

Applications 712 can include web browser or standalone client application 736, built-in application 738, and/or third-party application 740. Some examples of built-in application 738 include a contacts application, a browser application, a book reader application, a location application, a media application, a messaging application, and/or a game application. Third-party application 740 may include any application developed by an entity other than the vendor of the host operating system or platform, such as desktop software running on Microsoft Windows®, UNIX®, LINUX®, Apple Mac OS X®, or other suitable desktop operating system; or mobile software running on a mobile operating system such as Apple iOS®, Google Android®, Microsoft Windows Phone®, or other mobile operating system. In this example, third-party application 740 may invoke API calls 704 provided by operating system 720 to facilitate functionality described herein.

Applications 712 may utilize built-in operating system functions (e.g., kernel 718, services 722, and/or drivers 724), libraries (e.g., system libraries 742, API libraries 744, and other libraries 746), or frameworks/middleware 714 to create user interfaces to interact with users of the system. Alternatively, or in addition, interactions with a user may occur through presentation layer 710. In these systems, the application/module "logic" can be separated from the aspects of the application/module that interact with a user.

Some software architectures utilize virtual machines. In the example of FIG. 7, this is illustrated by virtual machine 706. A virtual machine creates a software environment where applications/modules can execute as if they were executing on a physical computing device (e.g., computing system 800 of FIG. 8). Virtual machine 706 can be hosted by a host operating system (e.g., operating system 720). The host operating system typically has a virtual machine monitor 760, which may manage the operation of virtual machine 706 as well as the interface with the host operating system (e.g., operating system 720). A software architecture executes within virtual machine 706, and may include operating system 734, libraries 732, frameworks/middleware 730, applications 728, and/or presentation layer 726. These layers executing within virtual machine 706 can operate similarly or differently to corresponding layers previously described.

Figure 8:
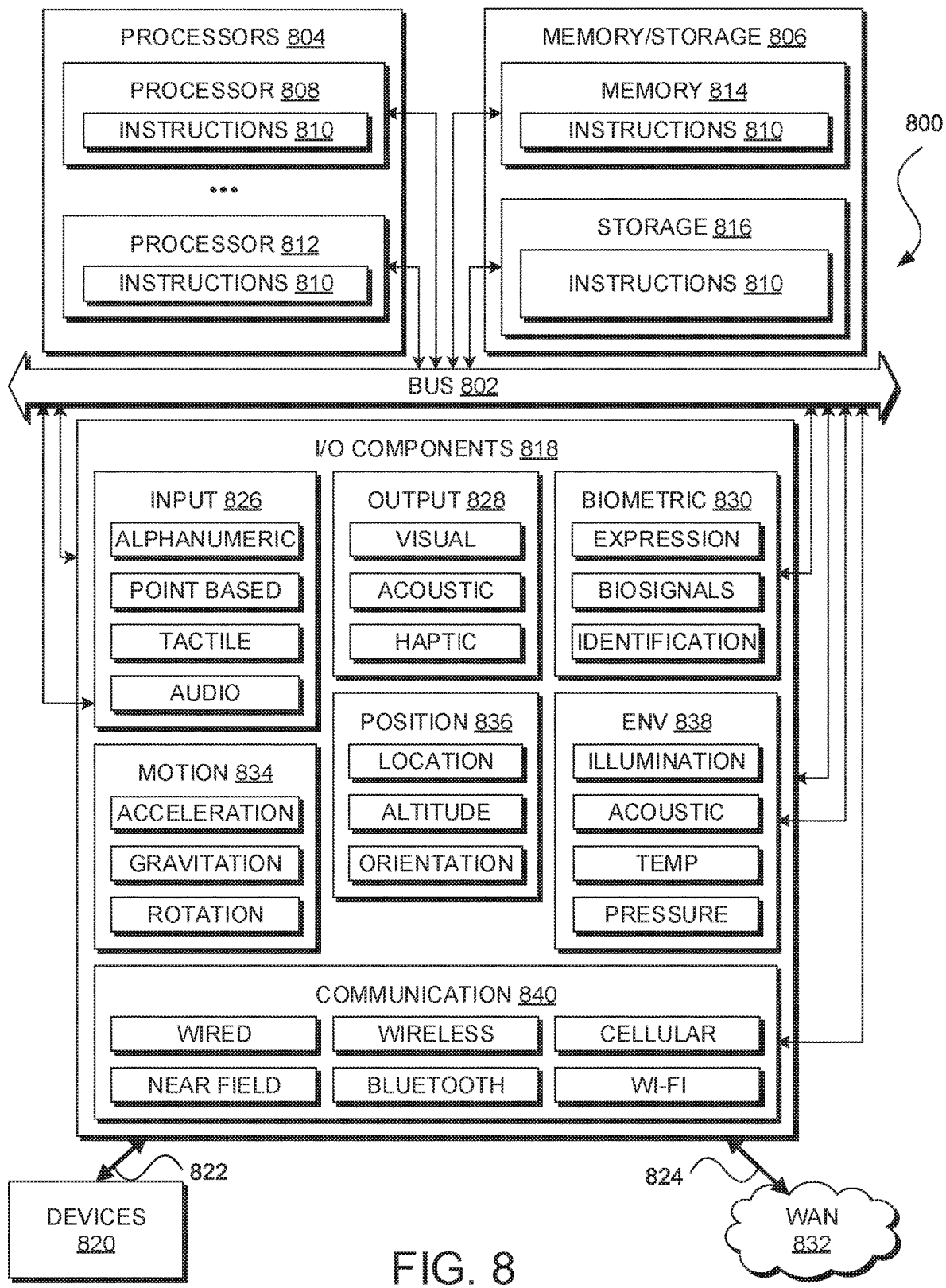
FIG. 8 illustrates an example of a computing device in accordance with an embodiment.

FIG. 8 shows an example of a computing device, computing system 800, in which various embodiments of the present disclosure may be implemented. In this example, computing system 800 can read instructions 810 from a computer-readable medium (e.g., a computer-readable storage medium) and perform any one or more of the methodologies discussed herein. Instructions 810 may include software, a program, an application, an applet, an app, or other executable code for causing computing system 800 to perform any one or more of the methodologies discussed herein. For example, instructions 810 may cause computing system 800 to execute process 400 of FIG. 4. Alternatively or in addition, instructions 810 may implement processing frameworks 122, 124, 126 or tools 162, 164, 166, and 168 of FIG. 1, processing framework 220, data virtualization layer 244, or services 212, 214, 216, 260, 262, 264, and 266 of FIG. 2, the graphical user interfaces of FIGS. 3A-3I; client applications 512, 514, and 516 or services 520 of FIG. 5; services 600 of FIG. 6, software architecture 700 of FIG. 7, and so forth. Instructions 810 can transform a general, non-programmed computer, such as computing system 800 into a particular computer programmed to carry out the functions described herein.

In some embodiments, computing system 800 can operate as a standalone device or may be coupled (e.g., networked) to other devices. In a networked deployment, computing system 800 may operate in the capacity of a server or a client device in a server-client network environment, or as a peer device in a peer-to-peer (or distributed) network environment. Computing system 800 may include a server, a workstation, a desktop computer, a laptop computer, a tablet computer, a netbook, a set-top box (STB), a personal digital assistant (PDA), an entertainment media system, a cellular telephone, a smart phone, a mobile device, a wearable device (e.g., a smart watch), a smart home device, other smart devices, a web appliance, a network router, a network switch, a network bridge, or any electronic device capable of executing instructions 810, sequentially or otherwise, that specify actions to be taken by computing system 800. Further, while a single device is illustrated in this example, the term "device" shall also be taken to include a collection of devices that individually or jointly execute instructions 810 to perform any one or more of the methodologies discussed herein.

Computing system 800 may include processors 804, memory/storage 806, and I/O components 818, which may be configured to communicate with each other such as via bus 802. In some embodiments, processors 804 (e.g., a central processing unit (CPU), a reduced instruction set computing (RISC) processor, a complex instruction set computing (CISC) processor, a graphics processing unit (GPU), a digital signal processor (DSP), an application specific integrated circuit (ASIC), a radio frequency integrated circuit (RFIC), another processor, or any suitable combination thereof) may include processor 808 and processor 812 for executing some or all of instructions 810. The term "processor" is intended to include a multi-core processor that may comprise two or more independent processors (sometimes also referred to as "cores") that may execute instructions contemporaneously. Although FIG. 8 shows multiple processors 804, computing system 800 may include a single processor with a single core, a single processor with multiple cores (e.g., a multi-core processor), multiple processors with a single core, multiple processors with multiples cores, or any combination thereof.

Memory/storage 806 may include memory 814 (e.g., main memory or other memory storage) and storage 816 (e.g., a hard-disk drive (HDD) or solid-state device (SSD) may be accessible to processors 804, such as via bus 802. Storage 816 and memory 814 store instructions 810, which may embody any one or more of the methodologies or functions described herein. Instructions 810 may also reside, completely or partially, within memory 814, within storage 816, within processors 804 (e.g., within the processor's cache memory), or any suitable combination thereof, during execution thereof by computing system 800. Accordingly, memory 814, storage 816, and the memory of processors 804 are examples of computer-readable media.

As used herein, "computer-readable medium" means an object able to store instructions and data temporarily or permanently and may include random-access memory (RAM), read-only memory (ROM), buffer memory, flash memory, optical media, magnetic media, cache memory, other types of storage (e.g., Erasable Programmable Read-Only Memory (EEPROM)) and/or any suitable combination thereof. The term "computer-readable medium" may include a single medium or multiple media (e.g., a centralized or distributed database, or associated caches and servers) able to store instructions 810. The term "computer-readable medium" can also include any medium, or combination of multiple media, that is capable of storing instructions (e.g., instructions 810) for execution by a computer (e.g., computing system 800), such that the instructions, when executed by one or more processors of the computer (e.g., processors 804), cause the computer to perform any one or more of the methodologies described herein. Accordingly, a "computer-readable medium" refers to a single storage apparatus or device, as well as "cloud-based" storage systems or storage networks that include multiple storage apparatus or devices. The term "computer-readable medium" excludes signals per se.

I/O components 818 may include a wide variety of components to receive input, provide output, produce output, transmit information, exchange information, capture measurements, and so on. The specific I/O components included in a particular device will depend on the type of device. For example, portable devices such as mobile phones will likely include a touchscreen or other such input mechanisms, while a headless server will likely not include a touch sensor. In some embodiments, I/O components 818 may include output components 826 and input components 828. Output components 826 may include visual components (e.g., a display such as a plasma display panel (PDP), a light emitting diode (LED) display, a liquid crystal display (LCD), a projector, or a cathode ray tube (CRT)), acoustic components (e.g., speakers), haptic components (e.g., a vibratory motor, resistance mechanisms), other signal generators, and so forth. Input components 818 may include alphanumeric input components (e.g., a keyboard, a touch screen configured to receive alphanumeric input, a photo-optical keyboard, or other alphanumeric input components), pointer-based input components (e.g., a mouse, a touchpad, a trackball, a joystick, a motion sensor, or other pointing instruments), tactile input components (e.g., a physical button, a touch screen that provides location and/or force of touches or touch gestures, or other tactile input components), audio input components (e.g., a microphone), and the like.

In some embodiments, I/O components 818 may also include biometric components 830, motion components 834, position components 836, or environmental components 838, or among a wide array of other components. For example, biometric components 830 may include components to detect expressions (e.g., hand expressions, facial expressions, vocal expressions, body gestures, or eye tracking), measure bio-signals (e.g., blood pressure, heart rate, body temperature, perspiration, or brain waves), identify a person (e.g., voice identification, retinal identification, facial identification, fingerprint identification, or electroencephalogram-based identification), and the like. Motion components 834 may include acceleration sensor components (e.g., accelerometer), gravitation sensor components, rotation sensor components (e.g., gyroscope), and so forth. Position components 836 may include location sensor components (e.g., a Global Position System (GPS) receiver component), altitude sensor components altimeters or barometers that detect air pressure from which altitude may be derived), orientation sensor components (e.g., magnetometers), and the like. Environmental components 838 may include illumination sensor components (e.g., photometer), temperature sensor components (e.g., one or more thermometers that detect ambient temperature), humidity sensor components, pressure sensor components (e.g., barometer), acoustic sensor components (e.g., one or more microphones that detect background noise), proximity sensor components (e.g., infrared sensors that detect nearby objects), gas sensors (e.g., gas detection sensors to detect concentrations of hazardous gases for safety or to measure pollutants in the atmosphere), or other components that may provide indications, measurements, or signals corresponding to a surrounding physical environment.

Communication may be implemented using a wide variety of technologies. I/O components 818 may include communication components 840 operable to couple computing system 800 to WAN 832 or devices 820 via coupling 824 and coupling 822 respectively. For example, communication components 840 may include a network interface component or other suitable device to interface with WAN 832. In some embodiments, communication components 840 may include wired communication components, wireless communication components, cellular communication components, Near Field Communication (NFC) components, Bluetooth components (e.g., Bluetooth Low Energy), Wi-Fi components, and other communication components to provide communication via other modalities. Devices 820 may be another computing device or any of a wide variety of peripheral devices (e.g., a peripheral device coupled via USB).

Moreover, communication components 840 may detect identifiers or include components operable to detect identifiers. For example, communication components 840 may include radio frequency identification (RFID) tag reader components, NFC smart tag detection components, optical reader components (e.g., an optical sensor to detect one-dimensional bar codes such as Universal Product Code (UPC) bar code, multi-dimensional bar codes such as Quick Response (QR) code, Aztec code, Data Matrix, Dataglyph, MaxiCode, PDF417, Ultra Code, UCC RSS-2D bar code, and other optical codes), or acoustic detection components (e.g., microphones to identify tagged audio signals). In addition, a variety of information may be derived via communication components 840, such as location via Internet Protocol (IP) geolocation, location via Wi-Fi signal triangulation, location via detecting an NFC beacon signal that may indicate a particular location, and so forth.

In various embodiments, one or more portions of WAN 832 may be an ad hoc network, an intranet, an extranet, a virtual private network (VPN), a local area network (LAN), a wireless LAN (WLAN), a wide area network (WAN), a wireless WAN (WWAN), a metropolitan area network (MAN), the Internet, a portion of the Internet, a portion of the Public Switched Telephone Network (PSTN), a plain old telephone service (POTS) network, a cellular telephone network, a wireless network, a Wi-Fi network, another type of network, or a combination of two or more such networks. For example, WAN 832 or a portion of WAN 832 may include a wireless or cellular network and coupling 824 may be a Code Division Multiple Access (CDMA) connection, a Global System for Mobile communications (GSM) connection, or another type of cellular or wireless coupling. In this example, coupling 824 may implement any of a variety of types of data transfer technology, such as Single Carrier Radio Transmission Technology (1×RTT), Evolution-Data Optimized (EVDO) technology, General Packet Radio Service (GPRS) technology, Enhanced Data rates for GSM Evolution (EDGE) technology, third Generation Partnership Project (3GPP) including 3G, fourth generation wireless (4G) networks, Universal Mobile Telecommunications System (UMTS), High-Speed Packet Access (HSPA), Worldwide Interoperability for Microwave Access (WiMAX) Long Term Evolution (LTE) standard, others defined by various standard-setting organizations, other long-range protocols, or other data transfer technology.

Instructions 810 may be transmitted or received over WAN 832 using a transmission medium via a network interface device (e.g., a network interface component included in communication components 840) and utilizing any one of several well-known transfer protocols (e.g., HTTP). Similarly, instructions 810 may be transmitted or received using a transmission medium via coupling 822 (e.g., a peer-to-peer coupling) to devices 820. The term "transmission medium" includes any intangible medium that is capable of storing, encoding, or carrying instructions 810 for execution by computing system 800, and includes digital or analog communications signals or other intangible media to facilitate communication of such software.

Throughout this specification, plural instances may implement components, operations, or structures described as a single instance. Although individual operations of one or more methods are illustrated and described as separate operations, one or more of the individual operations may be performed concurrently, and nothing requires that the operations be performed in the order illustrated. Structures and functionality presented as separate components in example configurations may be implemented as a combined structure or component. Similarly, structures and functionality presented as a single component may be implemented as separate components. These and other variations, modifications, additions, and improvements fall within the scope of the subject matter herein.

The embodiments illustrated herein are described in sufficient detail to enable those skilled in the art to practice the teachings disclosed. Other embodiments may be used and derived therefrom, such that structural and logical substitutions and changes may be made without departing from the scope of this disclosure. The Detailed Description, therefore, is not to be taken in a limiting sense, and the scope of various embodiments is defined only by the appended claims, along with the full range of equivalents to which such claims are entitled.

As used herein, the term "or" may be construed in either an inclusive or exclusive sense. Moreover, plural instances may be provided for resources, operations, or structures described herein as a single instance. Additionally, boundaries between various resources, operations, components, engines, and data stores are somewhat arbitrary, and particular operations are illustrated in a context of specific illustrative configurations. Other allocations of functionality are envisioned and may fall within a scope of various embodiments of the present disclosure. In general, structures and functionality presented as separate resources in the example configurations may be implemented as a combined structure or resource. Similarly, structures and functionality presented as a single resource may be implemented as separate resources. These and other variations, modifications, additions, and improvements fall within a scope of embodiments of the present disclosure as represented by the appended claims. The specification and drawings are, accordingly, to be regarded in an illustrative rather than a restrictive sense.

The invention claimed is:

1. A computer-implemented method, comprising:
   receiving, in a distributive processing framework comprising a data virtualization layer, a first data stream, via a network, from one or more first computing devices and a second data stream, via the network, from one or more second computing devices, the first data stream comprising a first data type and the second data stream comprising a second data type;
   integrating the first data stream and the second data stream into a data storage layer based on the first and second data type;
   responsive to integrating the first data stream and the second data stream into the data storage layer, determining that the first data stream comprises the first data type;
   responsive to determining that the first data stream comprises the first data type, exposing an optimized view into the data storage layer;
   determining a current dietary amount consumed within a predetermined time period;
   receiving a request from a user account to add a food item to a virtual shopping cart;
   determining an updated dietary amount predicted to be consumed within the time period based on the current dietary amount and a predicted dietary amount associated with the food item;
   storing the updated dietary amount into the exposed optimized view of the data storage ager;
   retrieving the updated dietary amount from the exposed optimized view of the data storage layer;
   determining that, the updated dietary amount exceeds a threshold dietary amount;
   generating a graphical interface comprising a graphical gauge element associated with the current dietary amount;
   causing the graphical interface comprising the graphical gauge element, to be displayed on a client device; and
   updating the graphic gauge element of the graphical interface to display information associated with the user account indicating that purchasing the food item exceeds the threshold dietary amount.

2. The computer-implemented method of claim 1, further comprising:
   identifying a substitute food item for the food item; and
   transmitting second information to the user account recommending purchase of the substitute food item.

3. The computer-implemented method of claim 2, further comprising:
   determining a second updated dietary amount based on the current dietary amount and a second predicted dietary amount associated with the substitute food item; and
   determining that the second updated dietary amount is below the threshold dietary amount.

4. The computer-implemented method of claim 1, further comprising:
   transmitting a plurality of diet plans to the user account;
   receiving a selection of a first diet plan of the plurality of diet plans; and
   determining a dietary condition based on the selection of the first diet plan.

5. The computer-implemented method of claim 4, wherein the dietary condition is a food allergy and the threshold dietary amount is zero.

6. The computer-implemented method of claim 4, wherein the user account is associated with a plurality of users and the dietary condition is an aggregate dietary condition for the plurality of users.

7. The computer-implemented method of claim 1, further comprising:
   transmitting a graphical element representing the current dietary amount in proportion to the threshold dietary amount.

8. The computer-implemented method of claim 7, further comprising:
   transmitting a second graphical element representing the updated dietary amount exceeding the threshold dietary amount.

9. The computer-implemented method of claim 1, further comprising:
   pre-loading nutritional information associated with the food item in response to receiving a request to add a second food item to the virtual shopping cart.

10. The computer-implemented method of claim 9, further comprising:
    pre-loading information associated with a dietary condition in memory in response to receiving the request to add the second food item to the virtual shopping cart.

11. The computer-implemented method of claim 1, wherein the first data type includes online transaction processing information of a transaction including the food item.

12. The computer-implemented method of claim 1, wherein the first data type includes image data captured by a camera associated with the user account, and wherein the method further comprises identifying the food item in the image data.

13. A system, comprising:
one or more processors; and
memory including instructions that, when executed by the one or more processors, cause the system to perform operations comprising:
receiving, in a distributive processing framework comprising a data virtualization layer, a first data stream, via a network, from one or more first computing devices and a second data stream, via the network, from one or more second computing devices, the first data stream comprising a first data type and the second data stream comprising a second data type;
integrating the first data stream and the second data stream into a data storage layer based on the first and second data type;
responsive to integrating the first data stream and second data stream into the data storage a per, determining that the first data stream comprises the first data type;
responsive to determining that the first data stream comprises the first data type, exposing an optimized view into the data storage layer;
determining a current dietary amount consumed within a predetermined time period;
receiving a request from a user account to add a food item to a virtual shopping cart;
determining an updated dietary amount predicted to be consumed within the time period based on the current dietary amount and a predicted dietary amount associated with the food item;
storing the updated dietary amount into the exposed optimized view of the data storage layer;
retrieving the updated dietary amount from the exposed optimized view of the data storage layer;
determining that the updated dietary amount exceeds a threshold dietary amount;
generating a graphical interface comprising a graphical gauge element associated with the current dietary amount;
causing the graphical interface comprising the graphical gauge element, to be displayed on a client device; and
updating the graphic gauge element of the graphical interface to display information associated with the user account indicating that purchasing the food item exceeds the threshold dietary amount.

14. The system of claim 13, wherein the first data type data includes sensor data relating to at least one of biting, chewing, or swallowing captured by a food intake monitor associated with the user account.

15. The system of claim 13, wherein the first data type data includes recipe information captured by a digital assistant device associated with the user account.

16. The system of claim 13, wherein the operations further comprise:
transmitting a recommendation to the user account including one or more food items of a recipe stored by the system for the user account.

17. A non-transitory computer-readable storage medium including instructions that, when executed by one or more processors of a computing system, cause the computing system to perform operations comprising:
receiving, in a distributive processing framework comprising a data virtualization layer, a first data stream, via a network, from one or more first computing devices and a second data stream, via the network, from one or more second computing devices, the first data stream comprising a first data type and the second data stream comprising a second data type;
integrating the first data stream and the second data stream into a data storage layer based on the first and second data type;
responsive to integrating the first data stream and second data stream into the data storage layer, determining that the first data stream comprises the first data type;
responsive to determining that the first data stream comprises the first data type, exposing an optimized view into the data storage layer;
determining a current dietary amount consumed within a predetermined time period;
receiving a request from a user account to add a food item to a virtual shopping cart;
determining an updated dietary amount predicted to be consumed within the time period based on the current dietary amount and a predicted dietary amount associated with the food item;
storing the updated dietary amount into the exposed optimized view of the data storage layer;
retrieving the updated dietary amount from the exposed optimized view of the data storage layer;
determining that the updated dietary amount exceeds a threshold dietary amount;
generating a graphical interface comprising a graphical gauge element associated with the current dietary amount;
causing the graphical interface comprising the graphical gauge element, to be displayed on a client device; and
updating the graphic gauge element of the graphical interface to display information associated with the user account indicating that purchasing the food item exceeds the threshold dietary amount.

18. The non-transitory computer-readable storage medium of claim 17, wherein the updated dietary amount is a target amount of one of a food group, a nutrient, a vitamin, or mineral to be consumed within a specified time period.

19. The non-transitory computer-readable storage medium of claim 17, wherein the operations further comprise:
identifying a substitute food item for the food item; and
transmitting second information to the user account recommending purchase of the substitute food item.

20. The non-transitory computer-readable storage medium of claim 19, wherein the operations further comprise:
receiving a second request from the user account to purchase the substitute food item; and
processing a transaction for the substitute food item.

* * * * *